US008779004B2

(12) United States Patent
Gore et al.

(10) Patent No.: US 8,779,004 B2
(45) Date of Patent: Jul. 15, 2014

(54) STABLE EMULSION FORMULATIONS

(75) Inventors: Anuradha Gore, Newbury Park, CA (US); Anne Navratil, Newbury Park, CA (US); Seshadri Neervannan, Irvine, CA (US); Christopher W. Spancake, Cary, NC (US); Roger Zanon, Carmarillo, CA (US)

(73) Assignee: Amgen, Inc., Thousand Oaks, CA (US)

( * ) Notice: Subject to any disclaimer, the term of this patent is extended or adjusted under 35 U.S.C. 154(b) by 1642 days.

(21) Appl. No.: 11/738,444

(22) Filed: Apr. 20, 2007

(65) Prior Publication Data
US 2007/0249520 A1 Oct. 25, 2007

Related U.S. Application Data

(60) Provisional application No. 60/793,825, filed on Apr. 20, 2006.

(51) Int. Cl.
| A01N 33/02 | (2006.01) |
| A61K 31/135 | (2006.01) |
| A61K 31/7034 | (2006.01) |
| A61K 31/428 | (2006.01) |
| A61K 31/65 | (2006.01) |
| A61K 31/43 | (2006.01) |
| A61K 47/18 | (2006.01) |
| A61K 31/423 | (2006.01) |
| A61K 31/7048 | (2006.01) |
| A61K 31/545 | (2006.01) |
| A61K 9/00 | (2006.01) |
| A61K 31/5513 | (2006.01) |
| A61K 9/107 | (2006.01) |

(52) U.S. Cl.
CPC ........... *A61K 9/0019* (2013.01); *A61K 31/7034* (2013.01); *A61K 31/428* (2013.01); *A61K 31/65* (2013.01); *A61K 31/43* (2013.01); *A61K 47/18* (2013.01); *A61K 31/423* (2013.01); *A61K 31/7048* (2013.01); *A61K 31/545* (2013.01); *A61K 31/5513* (2013.01); *A61K 9/1075* (2013.01)
USPC .......................................... 514/649

(58) Field of Classification Search
None
See application file for complete search history.

(56) References Cited

U.S. PATENT DOCUMENTS

| 5,688,938 A | 11/1997 | Brown et al. |
| 5,763,569 A | 6/1998 | Brown et al. |
| 5,858,684 A | 1/1999 | Nemeth et al. |

(Continued)

FOREIGN PATENT DOCUMENTS

| CN | 1451378 | 10/2003 |
| EP | 637237 | 2/1995 |

(Continued)

OTHER PUBLICATIONS

Harris et al. (Dec. 2004). Pharmacokinetics, pharmacodynamics, and safety of cinacalcet hydrochloride in hemodialysis patients at doses up to 200 mg once daily. p. 1070.*

(Continued)

*Primary Examiner* — Trevor Love
(74) *Attorney, Agent, or Firm* — Fitzpatrick, Cella, Harper & Scinto

(57) ABSTRACT

The present invention relates to injectable formulations of irritant agents, such as calcimimetics, that are pharmaceutically stable and demonstrate a reduced incidence of irritation, pain, phlebitis, precipitation and hemolysis upon injection.

46 Claims, 5 Drawing Sheets

(56) References Cited

U.S. PATENT DOCUMENTS

| | | | |
|---|---|---|---|
| 5,962,314 | A | 10/1999 | Brown et al. |
| 5,981,599 | A | 11/1999 | Moe et al. |
| 6,001,884 | A | 12/1999 | Nemeth et al. |
| 6,011,068 | A | 1/2000 | Nemeth et al. |
| 6,031,003 | A | 2/2000 | Nemeth et al. |
| 6,172,091 | B1 | 1/2001 | Cohen et al. |
| 6,211,244 | B1 | 4/2001 | Van Wagenen et al. |
| 6,313,146 | B1 | 11/2001 | Van Wagenen et al. |
| 6,342,532 | B1 | 1/2002 | Moe et al. |
| 6,362,231 | B1 | 3/2002 | Sakai et al. |
| 6,432,656 | B1 | 8/2002 | Del Mar et al. |
| 6,710,088 | B2 | 3/2004 | Moe et al. |
| 6,750,255 | B2 | 6/2004 | Sakai et al. |
| 6,908,935 | B2 | 6/2005 | Kelly et al. |
| 7,097,849 | B2 * | 8/2006 | Mishra et al. ............ 424/423 |
| 7,157,498 | B2 | 1/2007 | Dauban et al. |
| 7,176,322 | B2 | 2/2007 | Kelly et al. |
| 2002/0107406 | A1 | 8/2002 | Sakai et al. |
| 2003/0008876 | A1 | 1/2003 | Moe et al. |
| 2003/0144526 | A1 | 7/2003 | Sakai et al. |
| 2003/0176485 | A1 | 9/2003 | Sakai et al. |
| 2003/0199497 | A1 | 10/2003 | Ruat et al. |
| 2004/0006130 | A1 | 1/2004 | Shinagawa et al. |
| 2004/0077619 | A1 | 4/2004 | Kelly et al. |
| 2005/0020674 | A1 * | 1/2005 | Jenkins et al. ............ 514/488 |
| 2005/0032796 | A1 | 2/2005 | Shinagawa et al. |
| 2005/0101576 | A1 | 5/2005 | Whitehouse et al. |
| 2005/0107448 | A1 | 5/2005 | Shinagawa et al. |
| 2005/0143426 | A1 | 6/2005 | Kelly et al. |
| 2006/0135572 | A1 | 6/2006 | Shinagawa et al. |
| 2006/0276534 | A1 | 12/2006 | Martin et al. |

FOREIGN PATENT DOCUMENTS

| | | |
|---|---|---|
| EP | 933354 | 8/1999 |
| EP | 1258471 | 11/2002 |
| EP | 1275635 | 1/2003 |
| EP | 1281702 | 2/2003 |
| EP | 1296142 | 3/2003 |
| EP | 1308436 | 5/2003 |
| EP | 1553078 | 7/2005 |
| EP | 1576953 | 9/2005 |
| FR | 0511940 | 1/1921 |
| WO | WO-93/04373 | 3/1993 |
| WO | WO-94/18959 | 9/1994 |
| WO | WO-95/11221 | 4/1995 |
| WO | WO-96/12697 | 5/1996 |
| WO | WO-97/41090 | 11/1997 |
| WO | WO-99/13865 | 3/1999 |
| WO | WO 0001366 | 1/2000 |
| WO | WO-00/10531 | 3/2000 |
| WO | WO-01/34562 | 5/2001 |
| WO | WO-01/90069 | 11/2001 |
| WO | WO-01/97779 | 12/2001 |
| WO | WO-02/14259 | 2/2002 |
| WO | WO 02/059102 | 8/2002 |
| WO | WO-03/099776 | 12/2003 |
| WO | WO-03/099814 | 12/2003 |
| WO | WO-2004/017908 | 3/2004 |
| WO | WO-2004/094362 | 3/2004 |
| WO | WO-2004/106280 | 12/2004 |
| WO | WO-2006/117211 | 11/2006 |
| WO | WO-2006/123725 | 11/2006 |
| WO | WO-2007/027548 | 3/2007 |

OTHER PUBLICATIONS

Tonnesen. (2004). Photostability of drugs and drug formulations. p. 313.*
Mutscheler et al. (1995). Drug actions: basic principles and therapeutic aspects. p. 184. Accessible online at: http://books.google.com/books?id=IvN4mZxraMkC&pg=PA184&dq=procaine+or+benzocaine+anesthetic+injection&hl=en&ei=O5zAS--HJIaBIAeRhaXdBA&sa=X&oi=book_result&ct=result&resnum=9&ved=0CGwQ6AEwCA#v=onepage&q&f=false.*

Deau et al. (2003). Inhibition by propofol of intracellular calcium mobilization in cultured mouse pituitary cells. Anesth. Analg.; 97, 1325-1330.*
Mohler et al. (2006). Advanced therapy in hypertension and vascular disease. p. 302. Accessible online at http://books.google.com/books?hl=en&lr=&id=sCgURxhCJ-8C&oi=fnd&pg=PA300&dq=cinacalcet+calcium+channel+blocker&ots=cJAa3qasJn&sig=5dQvUFuledWunTPCGYE1z9DhaDo#v=onepage&q=cinacalcet&f=false.*
International Preliminary Report on Patentability for PCT/US2007/067155, dated Oct. 30, 2008. (11 pgs.).
Berge et al., "Pharmaceutical Salts", *J. Pharm. Sci.*, 66:1-19 (1977).
Brazeau et al., "Current Perspectives on Pain upon Injection of Drugs", *J. Pharm. Sci.*, 87:667-677 (1998).
Chen et al., "Vascular Calcification in Chronic Kidney Disease", *Semin. Nephrol.* 24:61-68 (2004).
Davio et al., "Precipitation of the renin inhibitor ditekirin[1] upon iv infusion; in vitro studies and their relationship to in vivo precipitation in the cynomolgus monkey", *Pharm. Res.*, 8:80-83 (1991).
Holick, "Noncalcemic actions of 1,25-dihydroxyvitamin D3 and clinical applications", *Bone*, 17:107S-111S (1995).
Holick et al., "Disorders of bone and mineral metabolism," Part 11, Chapter 335 "Calcium, Phosphorus, and bone metabolism: calcium-regulating hormones", pp. 1857-1870, in Kaspar et al., *Harrison's Principles of Internal Medicine*, New York: McGraw-Hill 1987.
Johnson et al., "Prediction of precipitation-induced phlebitis: a statistical validation of an in vitro model", *J. Pharm. Sci.*, 92:1574-1581 (2003).
Krzyzaniak et al., "Lysis of human red blood cells 2: effect of contact time on cosolvent induced hemolysis", *Int. J. Pharm.*, 152:193-200 (1997).
Krzyzaniak et al., "Lysis of human red blood cells. 4. Comparison of in vitro and in vivo hemolysis data", *J. Pharm. Sci.*, 86:1215-1217 (1997).
Lee et al., "An intravenous formulation decision tree for discovery compound formulation development", *Int. J. Pharm.*, 253:111-119 (2003).
Napaporn et al., "Assessment of the myotoxicity of pharmaceutical buffers using an in vitro muscle model: effect of pH, capacity, tonicity, and buffer type", *Pharm. Dev. Technol.*, 5:123-130 (2000).
Obeng et al., "In vitro dynamic method for evaluating the hemolytic potential of intravenous solutions", *J. Parenter. Sci. Technol.*, 43:167-173 (1989).
Powis et al., "Disposition of bisantrene in humans and rabbits: evidence for intravascular deposition of drug as a cause of phlebitis[1]", *Cancer Res.*, 43:925-929 (1983).
Proudfoot et al., "Biology of calcification in vascular cells: intima versus media", *Herz*, 26:245-251 (2001).
Reed et al., "Lysis of human red blood cells in the presence of various cosolvents", *J. Parenter. Sci. Technol.*, 39:64-69 (1985).
Reed et al., "Lysis of human red blood cells in the presence of various cosolvents. II. The effect of differing NaCl concentrations", *J. Parenter. Sci. Technol.*, 40:88-94 (1986).
Reed et al., "Lysis of human red blood cells in the presence of various cosolvents. III. The relationship between hemolytic potential and structure", *J. Parenter. Sci. Technol.*, 41:37-39 (1987).
Strickley, "Solubilizing excipients in oral and injectable formulations", *Pharm. Res.*, 21:201-230 (2004).
Stumpf et al., "Target cells for 1,25-dihydroxyvitamin D3 in intestinal trace, stomach, kidney, skin, pituitary, and parathyroid," *Science*, 206:1188-1190 (1979).
Ward et al., "Studies in phlebitis VI: • dilution-induced precipitation of amiodarone HCL", *J. Parenter. Sci. Technol.*, 47:161-165 (1993).
Ward et al., "Studies in phlebitis IV: injection rate and amiodarone-induced phlebitis", *J. Parenter. Sci. Technol.*, 47:40-43 (1993).
Ward et al., "Studies in phlebitis: detection and quantitation using a thermographic camera", *Pharm. Res.*, 8:76-79 (1991).

(56) References Cited

OTHER PUBLICATIONS

Ward et al., "Studies in phlebitis. II. Early detection of amiodarone-induced phlebitis in a rabbit model", *Pharm. Res.*, 8:801-803 (1991).
White et al., "Studies in phlebitis: III. Evaluation of diazepam and phenytoin", *Pharm. Res.*, 8:1341-1342 (1991).
Yalkowsky et al., "In vitro method for detecting precipitation of parenteral formulations after injection", *J. Pharm. Sci.*, 72:1014-1017 (1983).
Yalkowsky et al., "Formulation-related problems associated with intravenous drug delivery", *J. Pharm: Sci.*, 87:787-796 (1998).

* cited by examiner

*NOTE: The head-space in each vessel is constantly purged with $N_2$.

STABLE EMULSION FORMULATIONS

The present application claims the benefit of priority of U.S. Provisional Patent Application No. 60/793,825, which was filed Apr. 20, 2006. The entire text of the aforementioned application is incorporated herein by reference.

FIELD OF THE INVENTION

This invention relates generally to the field of medicine and, more specifically, to drug delivery compositions.

BACKGROUND OF THE INVENTION

Many drugs are introduced into the systemic circulation by intravenous (IV) injection to ensure rapid and complete bioavailability, and to transport them to their therapeutic target in the body. However, clinical use of these drugs may be limited if at their target dose the drugs are insoluble or poorly soluble in water in the desired injection volume. Such compounds are termed "hydrophobic", "lipophilic", or in their most difficult form, "amphiphobic".

If the drug at its target dose is not soluble in the desired injection volume and formulation vehicle, it becomes necessary to solubilize the drug to proceed with product development. The solubilization techniques for injectable formulations include pH adjustment, mixed aqueous/organic cosolvents, organic solvent mixtures, cyclodextrin complexation, liposomes, polymeric gels, and combinations of such techniques. Strickley, R. Pharm. Res. 21, 201-230, 2004. Ionizable drug molecules can be solubilized to the desired concentration by pH adjustment if the drug's pKa is sufficiently different from the formulation pH value. The solution pH can be controlled by either selecting the salt form of the drug, strong acids/bases, or a buffer. Where a buffer is used, the buffer concentration must be high enough to maintain the desired pH, but must be balanced by in vivo tolerability considerations. Napaporn, J. et al. Pharm. Dev. Tech. 5: 123-130 (2000). When pH adjustment alone is insufficient to achieve the desired concentration of the drug in solution, the combination of an aqueous solution and a water-soluble organic solvent/surfactant can be used in injectable formulations. Lee, Y-C. et al. Intl. J. Pharm. 253: 111-119 (2003). Moderately hydrophobic drugs can be solubilized by incorporating them into liposomes, closed spherical vesicles composed of outer lipid bilayer membranes and an inner aqueous core. In some instances the drug becomes encapsulated or intercalated within the liposome. Hydrophobic drugs can also be solubilized by liposomes if the drug molecule becomes an integral part of the lipid bilayer membrane by dissolving in the lipid portion of the lipid bilayer.

The drug is considered "challenging" if the drug is not solubilized by pH modification, cosolvents, complexation or combinations of these approaches. Surfactants, such as Cremophor EL, Cremophor RH 60, and polysorbate 80, can be used to solubilize some of the most water-insoluble drugs. These formulations can be prepared to contain concentrated drug solutions in an organic solvent that is diluted prior to intravenous administration. However, the limitations of these approaches include the possibility of precipitation of the drug, pain, inflammation, hemolysis, phlebitis, as well as deleterious effects on drug stability.

SUMMARY OF THE INVENTION

The present invention provides anti-irritant emulsion formulations suitable for intravenous injection capable of reducing, inhibiting, or eliminating precipitation of the drug, pain, inflammation, hemolysis, or phlebitis.

In one aspect, the invention provides pharmaceutical formulations, comprising an oil phase containing a hydrophobic or amphiphilic irritant agent; a phospholipid emulsifier; and an aqueous phase containing a charge stabilizer, wherein the stabilizer has pH<pKa of the irritant agent if the agent is acidic, or the stabilizer has pH>pKa of the irritant agent if the agent is basic, wherein the formulation is stable and has a protective effect against irritation caused by the irritant agent.

In one aspect, the irritant agent can be acidic. In another aspect, it can be basic.

In one aspect, the charge stabilizer can be a buffer. For example, the buffer can be selected from the group consisting of diethanolamine, glycine, citrate, acetate, histidine, phosphate, carbonate, meglumine, N-methyl glucamine and tris (hydroxymethyl)aminomethane (TRIS) buffers. In another aspect, the charge stabilizer is an acid or a salt thereof. The acid or the salt thereof can be selected from the group consisting of hydrochloric acid, tartaric acid, benzoic acid, citric acid, and salts thereof. In a further aspect, the charge stabilizer is NaOH or KOH.

In one aspect, the phospholipid emulsifier can be an egg lecithin, egg yolk phospholipids, soy lecithin or soybean phospholipids.

In one aspect, the oil phase can comprise a vegetable oil or a hydrogenated vegetable oil. The vegetable or the hydrogenated vegetable oil can be selected from the group consisting of peanut oil, corn oil, castor oil, cottonseed oil, soybean oil, olive oil, safflower oil, peppermint oil, coconut oil and palm seed oil. In another aspect, the oil phase can be selected from the group consisting of beeswax, vitamin E, oleic acid, medium chain monoglycerides, diglycerides, triglycerides, structured triglycerides, and mixtures thereof.

The invention further provides formulations, wherein the hydrophobic or amphiphilic irritant agent is selected from the group consisting of penicillin, an aminoglycoside, aminocyclitrol, tetracycline, macrolide antibiotics, cephalosporin antibiotics, antimalarials, antiprotozoals, antihelmintics, antineoplastics, benzodiazepines, phenothiazines, anesthetics, skeletal muscle relaxants, antirheumatics, adrenergic agents, peptide drugs, protein drugs, and nonsteroidal anti-inflammatory agents.

In one aspect, the invention provides pharmaceutical formulations comprising an oil phase from 5 to 30% by weight containing a hydrophobic or amphiphilic calcimimetic compound from 0.0001 to 11% by weight; a phospholipid emulsifier from 0.2 to 5% by weight; and an aqueous phase containing a charge stabilizer, wherein the formulation is stable and has a protective effect against irritation caused by the calcimimetic compound.

In one aspect, the calcimimetic compound can be a compound of Formula I

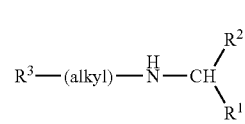

I wherein all substituents are as defined in Detailed Description.

In another aspect, the calcimimetic compound used in the compositions of the invention can be a compound of Formula II

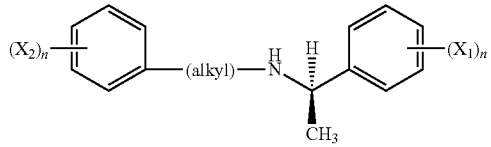

wherein all substituents are as defined in Detailed Description.

In one aspect, the calcimimetic compound used in the compositions of the invention can be N-(3-[2-chlorophenyl]-propyl)-R-α-methyl-3-methoxybenzylamine or a pharmaceutically acceptable salt thereof.

In another aspect, the calcimimetic compound can be a compound of Formula III and pharmaceutically acceptable salts thereof,

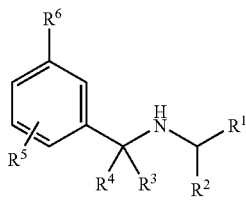

wherein all substituents are as defined in Detailed Description of the Invention.

In one aspect, the calcimimetic compound used in the compositions of the invention can be N-((6-(methyloxy)-4'-(trifluoromethyl)-1,1'-biphenyl-3-yl)methyl)-1-phenylethanamine, or a pharmaceutically acceptable salt thereof.

In certain examples, the calcimimetic compound is 1-(6-(methyloxy)-4'-(trifluoromethyl)-3-biphenylyl)-N-(1-phenylethyl)ethanamine, or a pharmaceutically acceptable salt thereof.

Some of the calcimimetic compounds disclosed herein have the Formula IV

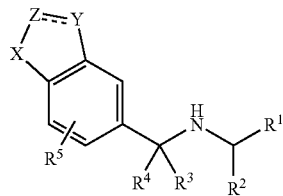

and pharmaceutically acceptable salts thereof, wherein all substituents are as defined in Detailed Description of the Invention.

Other examples of calcimimetic compounds described herein have the Formula V:

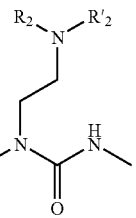

or a pharmaceutically acceptable salt thereof, wherein all substituents are as defined in Detailed Description of the Invention.

Specific examples of calcimimetic compounds of Formula V include is 3-(1,3-benzothiazol-2-yl)-1-(3,3-diphenylpropyl)-1-(2-(4-morpholinyl)ethyl)urea and N-(4-(2-((((3,3-diphenylpropyl)(2-(4-morpholinyl)ethyl)amino)carbonyl)amino)-1,3-thiazol-4-yl)phenyl)methanesulfonamide or pharmaceutically acceptable salt thereof. Other exemplary calcimimetic compounds have the formula of Formula VI:

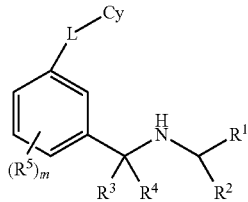

or a pharmaceutically acceptable salt thereof, wherein all substituents are as defined in Detailed Description of the Invention.

Specific examples of compounds of Formula VI include is N-(2-chloro-5-(((-1-phenylethyl)amino)methyl)phenyl)-5-methyl-3-isoxazolecarboxamide; and N-(2-chloro-5-(((-1-phenylethyl)amino)methyl)phenyl)-2-pyridinecarboxamide, or a pharmaceutically acceptable salt thereof.

Any of the specific compounds described herein may be the R enantiomer, the S enantiomer. In preparations of the invention, the emulsions may be prepared using the R enantiomer, the S enantiomer or a mixed population of R and S enantiomers.

In one aspect, the calcimimetic compound can be present in an amount from 0.001-110 mg/mL. Thus, in one aspect the calcimimetic compound can be present in a concentration of any integer (whole or particle) between 0.001 and 110 mg/mL or even greater. In some examples the calcimimetic compound is present in an amount of from 0.2 to 50 mg/mL.

In one aspect, calcimimetic-containing formulations of the invention can comprise a phospholipid, wherein the phospholipid emulsifier can be an egg lecithin, egg yolk phospholipids, soy lecithin or soybean phospholipids. The identity of the phospholipid is not important and the phospholipid may be from a natural origin or may be a synthetic emulsifier. In one aspect of the invention the emulsions created are such that the overall charge of the droplet in the emulsion is a negative charge. For example, this negative charge can be conferred by the phospholipids emulsifier content in the emulsion. However, it is contemplated that other agents may be added to the composition in order to stabilize the charge and or to render the overall charge of the emulsion droplets more negative. Thus the compositions of the invention are characterized as negatively charged stabilized emulsions containing a given drug.

The charge stabilizer can be TRIS buffer in a concentration from 5 to 20 mM or, for example, diethanolamine buffer from 0.05 to 0.3% by weight. In one aspect, the formulations of the invention can further comprise glycerol. In one aspect, pH of the formulation can be from 7 to 9.5, or from 7.5 to 9.0, or from 8.0 to 9.5, or from 8.5 to 9.5. In one aspect, the formulation of the invention can further comprise at least one preservative, antioxidant, buffering agent, acidifying agent, alkalizing agent, antibacterial agent, antifungal agent, solubility enhancing agent, complexation enhancing agent, organic solvent, electrolyte, salt, stabilizer, tonicity modifier, antifoaming agent, or a combination thereof.

In one aspect, the stabilizer can be sodium oleate, oleic acid, linoleic acid, stearic acid or palmetic acid. In certain embodiments, the negatively charged emulsions are stabilized by the addition of a stabilizer such as a salt of a fatty acid. In exemplary embodiments, the stabilizer is may be a C10-C20 fatty acid. Thus, in exemplary embodiments, the compositions of the invention are stabilized with the addition of sodium decanoate (a C10 saturated fatty acid); sodium laurate (a C12 saturated fatty acid); sodium myristate (a C14 saturated fatty acid); sodium palmitate (a C16 saturated fatty acid); sodium stearate (a C18 saturated fatty acid); sodium icosanoate (a C20 saturated fatty acid); sodium behenate (C22 saturated fatty acid): or an unsaturated fatty acids of carbon length C10-C22, such as for example sodium myristoleate (a C14 mono-unsaturated fatty acid): sodium palmitoleate (a C16 mono-unsaturated fatty acid), a sodium oleate (a C18 mono-unsaturated fatty acid), sodium linoleate (a C18 diunsaturated fatty acid), sodium alpha linolenate (a C18 tri unsaturated fatty acid), sodium arachidonate (a C20 polyunsaturated fatty acid that contains 4 double bonds), sodiym eicosapentanoate (a C20 polyunsaturated fatty acid that contains 5 double bonds) and the like. While sodium is mentioned above as the cation, it should be understood that other cations may be used such as e.g., potassium. In certain exemplary embodiments, the emulsions are stabilized with sodium oleate.

In one aspect, the formulations can be stable at temperatures from 5° C. to 40° C. In another aspect, the formulations are stable after autoclaving. In one aspect, the formulations of the invention can further comprise one or more local anesthetic agents, for example, benzocaine or procaine.

The invention further provides different methods of administering the formulations of the invention to a subject in need thereof. In one aspect, the administration is intravenous. In one aspect, the formulations can be administered via infusion. In another aspect, the formulation can be administered by bolus injection.

The invention provides methods of preparing the formulations of the invention. In one aspect, the methods can comprise the following steps:
 (a) mixing the aqueous phase and the charge stabilizer;
 (b) dissolving the irritant agent in the oil phase
 (c) dissolving/dispersing the emulsifier in the oil phase
 (d) mixing the oil phase from step (b) and the aqueous phase from step (a);
 (e) homogenizing the formulation; and
 (f) optionally adjusting pH.

A person skilled in the art would understand that steps (a), (b) (c) and (d) can be performed in any order; indeed all the components may be mixed together in one step and then homogenized to form an emulsion. In one aspect, the irritant agent can be a calcimimetic compound suitable in the emulsions of the invention.

The invention further provides methods of treating a disease using the formulations of the invention. In general, the pharmaceutical formulations of the invention can be used to treat any disease or condition for which the irritant therapeutic agent is suitable. For example, calcimimetic-containing emulsion formulations of the invention can be used to treat any disease for which a calcimimetic compound can be used. In one aspect, the invention provides methods of treating hyperparathyroidism, osteoporosis or vascular calcification, the method comprising administering the formulations of the invention to a subject in need thereof.

DETAILED DESCRIPTION OF THE INVENTION

I. Definitions

Figure 1:
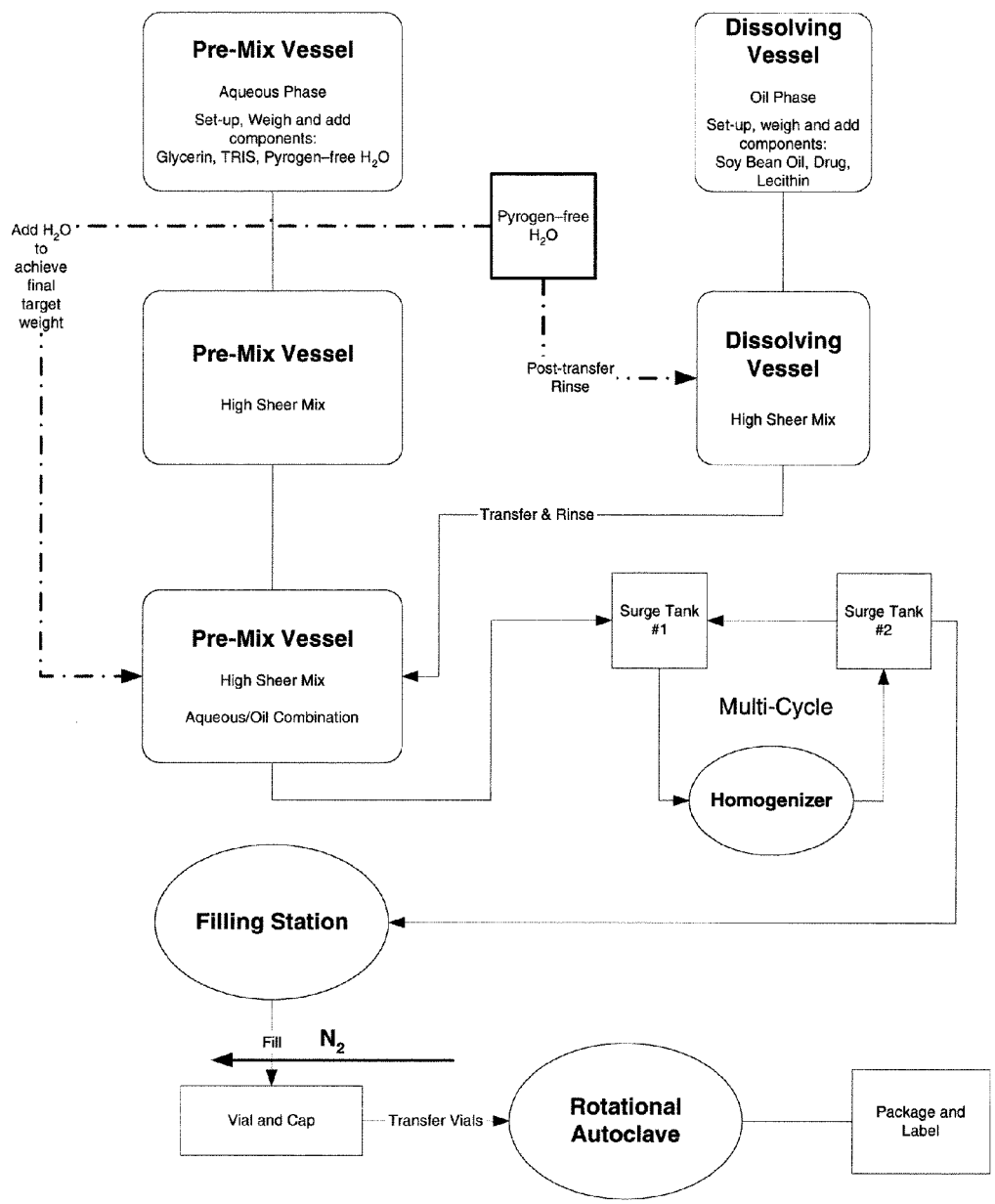
FIG. 1 schematically represents the manufacturing process flow chart for preparation of the formulations of the invention.

The term "emulsion" or "emulsion formulation" means a colloidal dispersion of two immiscible liquids in the form of droplets, whose diameter, in general, is between 0.1 and 3.0 microns. An emulsion is denoted by the symbol O/W if the continuous phase is an aqueous solution and by W/O if the continuous phase is an oil. Other examples of emulsions such as O/W/O include oil droplets contained within aqueous droplets dispersed in a continuous oil phase.

An "emulsifier" refers to a compound that prevents the separation of the injectable emulsion into individual oil and aqueous phases. Emulsifiers useful in the present invention generally are (1) compatible with the other ingredients of the stable emulsions of the present invention, (2) do not interfere with the stability or efficacy of the drugs contained in the emulsions, (3) are stable and do not deteriorate in the preparation, and (4) are non-toxic.

Suitable emulsifiers include, but are not limited to, propylene glycol mono- and di-fatty acid esters, polyoxyethylene sorbitan fatty acid esters, polyoxyethylene fatty acid esters, polyoxyethylene-polyoxypropylene co-polymers and block co-polymers, salts of fatty alcohol sulphates, sorbitan fatty acid esters, esters of polyethylene-glycol glycerol ethers, oil and wax based emulsifiers, glycerol monostearate, glycerine sorbitan fatty acid esters and phospholipids.

A "phospholipid" refers to a triester of glycerol with two fatty acids and one phosphate ion. Exemplary phospholipids useful in the present invention include, but are not limited to, phosphatidyl chlorine, lecithin (a mixture of choline ester of phosphorylated diacylglyceride), phosphatidylethanolamine, phosphatidylglycerol, phosphatidic acid with about 4 to about 22 carbon atoms, and more generally from about 10 to about 18 carbon atoms and varying degrees of saturation. The phospholipids can have any combination of fatty acid as its fatty acyl side chain, for example, the phospholipids can have a saturated fatty acid such as a decanoic acid, lauric acid, myristic acid, palmitic acid, stearic acid, icosanoic acid, (a C20 saturated fatty acid); sodium behenic acid, or an unsaturated fatty acid such as myristoleic acid, palmitoleic acid, oleic acid, sodium linoleic acid, alpha linolenic acid, sodium arachidonic acid, eicosapentanoic acid, and the like. The two fatty acyl residues on the phospholipids may be the same or they may be different fatty acids. The phospholipid component of the drug delivery composition can be either a single phospholipid or a mixture of several phospholipids. The phospholipids should be acceptable for the chosen route of administration.

In one aspect, the phospholipids used as emulsifiers in the present invention are naturally occurring phospholipids from a natural origin. For example, naturally occurring lecithin is a mixture of the diglycerides of stearic, palmitic, and oleic acids, linked to the choline ester of phosphoric acid, commonly called phosphatidylcholine, and can be obtained from a variety of sources such as eggs and soya beans. Soy lecithin and egg lecithin (including hydrogenated versions of these compounds) have been characterized in various compositions and are generally recognized to be safe, have combined emulsification and solubilization properties, and tend to be broken down into innocuous substances more rapidly than most synthetic surfactants. Commercially available soya phospholipids include the Centrophase and Centrolex products marketed and sold by Central Soya, Phospholipon from Phospholipid GmbH, Germany, Lipoid by Lipoid GmbH, Germany, and EPIKURON by Degussa.

Synthetic phospholipids, diacylglycerols and triacylglyercols also may be used as emulsifiers herein. For example, common synthetic lipids known to be useful as typical emulsifiers include, but are not limited to diacylglycerols such as 1,2-Dilauroyl-sn-glycerol (DLG), 1,2-Dimyristoyl-sn-glycerol (DMG), 1,2-Dipalmitoyl-sn-glycerol (DPG), 1,2-Distearoyl-sn-glycerol (DSG); phosphatidic acids such as 1,2-Dimyristoyl-sn-glycero-3-phosphatidic acid, sodium salt (DMPA,Na), 1,2-Dipalmitoyl-sn-glycero-3-phosphatidic acid, sodium salt (DPPA,Na), 1,2-Distearoyl-sn-glycero-3-phosphatidic acid, sodium salt-(DSPA,Na); phosphatidylcholines such as 1,2-Dilauroyl-sn-glycero-3-phosphocholine (DLPC), 1,2-Dimyristoyl-sn-glycero-3-phosphocholine (DMPC), 1,2-Dipalmitoyl-sn-glycero-3-phosphocholine (DPPC), 1,2-Dipalmitoyl-sn-glycero-3-phosphocholine (DPPC), 1,2-Distearoyl-sn-glycero-3-phosphocholine (DSPC), 1,2-Distearoyl-sn-glycero-3-phosphocholine (DSPC); phosphatidylethanolamines such as 1,2-Dilauroyl-sn-glycero-3-phosphoethanolamine (DLPE), 1,2-Dimyristoyl-sn-glycero-3-phosphoethanolamine (DMPE), 1,2-Dipalmitoyl-sn-glycero-3-phosphoethanolamine (DPPE), 1,2-Distearoyl-sn-glycero-3-phosphoethanolamine (DSPE); phosphatidylclyerols such as 1,2-Dilauroyl-sn-glycero-3-phosphoglycerol, sodium salt (DLPG), 1,2-Dimyristoyl-sn-glycero-3-phosphoglycerol, sodium salt (DMPG), 1,2-Dimyristoyl-sn-glycero-3-phospho-sn-1-glycerol, ammonium salt (DMP-sn-1-G,NH4), 1,2-Dipalmitoyl-sn-glycero-3-phosphoglycerol, sodium salt (DPPG,Na), 1,2-Distearoyl-sn-glycero-3-phosphoglycerol, sodium salt (DSPG,Na), 1,2-Distearoyl-sn-glycero-3-phospho-sn-1-glycerol, sodium salt (DSP-sn-1G,Na), phosphatidylserines such as 1,2-Dipalmitoyl-sn-glycero-3-phospho-L-serine, sodium salt (DPPS,Na). The emulsifier composition can be made up of mixtures of the aforementioned phospholipids as well as phosphatidylinositols, cardiolipins. In addition, it is contemplated that mixed chain phospholipids also will be useful synthetic phospholipids emulsifiers for use herein. Such mixed chain phospholipids include, for example, 1-Palmitoyl-2-oleoyl-sn-glycero-3-phosphocholine (POPC), 1-Palmitoyl-2-oleoyl-sn-glycero-3-phosphoglycerol, sodium salt (POPG,Na), 1-Palmitoyl-2-oleoyl-sn-glycero-3-phosphoglycerol, ammonium salt (POPG,NH4). Additionally, lysophospholipids (i.e., phospholipids in which one of the two fatty acyl residues of the phospholipids is absent) may be useful emulsifiers. Exemplary lysophospholipids include 1-Palmitoyl-2-lyso-sn-glycero-3-phosphocholine (P-lyso-PC) and 1-Stearoyl-2-lyso-sn-glycero-3-phosphocholine (S-lyso-PC). One or more of the phospholipids also may be PEGylated.

The amount of phospholipids, by weight, in the emulsions of the present invention may be within a range of about 0.1% to about 5%. In certain embodiments, the phospholipids in the emulsions are at a concentration, by weight, about 0.1%, 0.25%, 0.5%, 1.0%, 1.5%, 2%, 2.5%, 3%, 3.5%, 4%, 4.5%, or 5%.

"Aqueous phase", as used herein, means a water-containing liquid which can contain pharmaceutically acceptable additives such as acidifying, alkalizing, buffering, chelating, complexing and solubilizing agents, antioxidants and antimicrobial preservatives, humectants, suspending and/or viscosity modifying agents, tonicity and wetting or other biocompatible materials.

"Oil" refers to an organic liquid of mineral, vegetable, animal, essential or synthetic origin, including, for example, aliphatic or wax-based hydrocarbons, aromatic hydrocarbons or mixed aliphatic and aromatic hydrocarbons.

The term "therapeutic agent" describes any natural or synthetic compound which has a biological activity.

"Irritant agent", as used herein, refers to any natural or synthetic compound capable of causing irritation, hemolysis, precipitation, phlebitis, or pain upon injection. Representative classes of irritant agents include, for example, penicillin, aminoglycoside, aminocyclitrol, tetracycline, macrolide and cephalosporin antibiotics, antimalarials, antiprotozoals, antihelmintics, antineoplastics, benzodiazepines, phenothiazines, anesthetics, skeletal muscle relaxants, antirheumatics, adrenergic agents, peptide and protein drugs, calcimimetics and nonsteroidal anti-inflammatory agents. Brazeau G. et al., J. Pharm. Sci. 87(6): 667-677, 1998. The present invention is directed to those amphiphilic or hydrophobic irritant agents that are capable of being formulated in the formulations of the invention.

The term "compound" refers to any active compound suitable for the formulations of the invention or its pharmaceutically acceptable salt. For example, the term "cinacalcet" encompasses not only cinacalcet freebase, but also all pharmaceutically acceptable salts.

In the stable emulsion compositions of the present invention, some or all of the components other than the drug being delivered in the emulsion composition (e.g., an emulsifier, a stabilizer, and an oil phase) are each safe, or well tolerated, and in one example, acceptable by the FDA for intravenous injection.

Components that are regarded as "safe" are those that do not cause undesired systemic reactions such as anaphylactic shock in patients.

Components that are "acceptable by the FDA" are those that have been used in intravenous injection products approved by the FDA as of the filing date of the present application, and are used at a concentration comparable to those used in FDA approved products.

In specific examples, some or all of the components of the stable emulsions (other than the drug being delivered) are generally regarded as safe for use in intravenous injections by a drug regulatory authority. Components that are "generally regarded as safe for use in intravenous injections by a drug regulatory authority" are those that have been used in intravenous injection products approved by the FDA or a drug regulatory authority in Europe, Japan, Australia and other jurisdictions as of the filing date of the present application, and is being used at a concentration comparable to those used in the products approved by the FDA in the United States or by a drug regulatory authority in other jurisdictions.

The term "hemolysis" refers to the loss of integrity of the red blood cell membrane with the release of the cellular components into the plasma. The resulting increase in hemoglobin concentration may lead to a number of symptoms including fever, chills, abdominal and back pain, shortness of breath, prostration and shock. High plasma concentrations of hemoglobin can lead to plaque formation and the clogging of renal tubules, thereby affecting kidney function, or produce congestion in the reticuloendothelial cells of the spleen and liver causing splenomegaly and jaundice, respectively.

"Phlebitis", or "thrombophlebitis", as used herein, refers to an inflammation of the vein wall and is characterized by clinical observations of pain tenderness, edema, erythema, and a local temperature increase. Phlebitis can cause thrombus formation, which can ultimately lead to death. It can result from mechanical irritation, chemical irritation, or as a pharmacological response by the vein wall cells to the irritant agent. In one example, the emulsions are such that they do not produce an irritant effect when administered into the vein, meaning that the composition as delivered when administered intravenously, does not cause substantial irritation at the injection site, as evident by, for example, thickened skin, necrotic skin, local redness, local swelling, venous dilation with blood clog formation, or venous embolism with subcutaneous inflammation.

"Pain", as used herein, includes burning, itching, stinging or aching, and may or may not be associated with cell or tissue damage such as phlebitis.

"Precipitation" includes precipitation of the irritant agent within the vein upon dilution or injected into the bloodstream. If a drug precipitates in the vein, the potential for venous irritation increases, due to mechanical irritation and to prolonged drug exposure at the vein wall.

The term "protective effect" as used herein, refers to reduction, elimination, or alleviation of symptoms of irritation, pain, phlebitis, hemolysis and precipitation.

The term "stable emulsion" or "stable emulsion formulation", as used herein, refers to a system wherein repulsive forces exist among the droplets. The forces can arise from a number of sources: (i) Van der Waals forces, (ii) electrostatic forces; (iii) solvent forces; (iv) steric forces. In general, emulsions are stabilized either by steric or electrostatic repulsion, depending on the nature of the surfactant. Steric forces are repulsive in nature and arise when long-chain hydrophilic macromolecules are absorbed or grafted to the colloid surface. Electrostatic forces are negative in nature and depend on the square of the zeta potential (the potential surrounding the droplet at the plane of hydrodynamic shear). Electrolytes modify the zeta potential by absorbing to the droplet surface and screening the droplet charges. In one aspect, stable emulsion is emulsion capable of maintaining pH from 0.00 to 1.75 units of the starting pH with the droplet size with d(90) below 1 μm. In another aspect, stable emulsion is capable of keeping its protective effect from any time long enough for the emulsion to be prepared and to be administered to a subject in need thereof to several years.

In one aspect, the compositions of the invention are both chemically and physically stable. A physically stable emulsion of the invention is one which can be stored under appropriate conditions for at least 1 month without increase in average droplet size by more than 100%, or evidence of phase separation or oil droplet aggregation (coalescence). In certain embodiments, the average size of oil droplets of an emulsion of the present invention does not increase by more than about 10%, 20%, 25%, 30%, 40%, 50%, 75%, 100%, 125%, 150%, 175%, or 200% under appropriate storage conditions for at least 1, 2, 3, 4, 5, 6, 9, 12, 15, 18, or 24 months.

"Chemically stable" emulsions of the invention are ones in which the concentration of the active component (i.e., the drug being delivered) does not change by about 20% under appropriate storage conditions for at least 1 month. In certain embodiments, the drug concentration in an emulsion of the present invention does not change by about 5%, 10%, 15% or 20% under appropriate storage conditions for at least 1, 2, 3, 4, 5, 6, 9, 12, 15, 18, or 24 months.

In one example, the stable emulsion compositions of the invention are stable over a wide range of temperatures, e.g., −20° C. to 40° C. The compositions of the invention may be stored at about 5° C. to about 25° C.

"Charge stabilizer" refers to any agent that contributes to the emulsion stability by increasing repulsive forces existing among the droplets. For example, it can be an acid, a base, or a buffer for pH adjustment of the formulations.

The term "by weight" refers herein to the total weight of the formulation. For example, the term "an oil phase from 1 to 30% by weight" refers to the proportion of the oil phase in the whole formulation.

The term "bolus" or "bolus injection" refers to a single dose of a therapeutic agent given to a subject over a short period of time.

The term "infusion" refers to a method of putting therapeutic agents into a blood stream over a period of time.

In certain aspects of the invention the stable emulsion formulations are prepared for injectable delivery. In one aspect, the emulsions can be made of sub-micron size droplets. A "sub-micron size droplet" refers to droplet in the emulsion that has an average diameter of less than 1 micron as measured by conventional sizing techniques such as laser light scattering spectrometry. In certain embodiments, the emulsion contains droplets of the drug compositions that have an average diameter of less than 500, 450, 400, 350, 300, or 250 nm. Oil droplets of sub-micron size are desired for the safe passage of these droplets in, the capillary blood vessel in the circulation. In some defined aspects droplets are less than 5 microns in diameter. The compositions of the invention may need to be prepared in a sterilized formulation. An effective method of sterilization that is well-known in the art is filtration through a 0.2 micron sized filter membrane. Thus, in certain embodiments, the droplets of the emulsion compositions of the invention have an average diameter that is less than 0.2-micron (200 nm). Thus, in exemplary, but non-limiting embodiments, the emulsion droplets have an average diameter of less than about 150, 100, 75, 50, 25, 20, 15, or 10 nm.

Abbreviations
SBO: Soybean oil
MCT: Medium chain (C8-C10) triglycerides
STG: Structured triglycerides
MCM: Medium chain (C8-C10) monoglyderides
EYP: Egg Yolk Phospholipids, also referred to as egg lecithin
DEA: Diethylamine
TRIS: Trometamine
d(4,3): Volume corrected mean
d(90): 90% percentile for particle size, a particle size such that 90% of particles have a size below this value
REV: Rabbit ear vein
IV: Intravenous

II. In Vitro and In Vivo Screening Methods for Evaluation of Irritation, Phlebitis, Hemolysis, and Pain A number of tests exists that help to evaluate whether a particular therapeutic agent may cause irritation, hemolysis, precipitation, phlebitis, or pain upon injection.

The rabbit ear model is the most often used animal model for screening formulations associated with intravenous injection, and the rabbit ear vein is considered the most convenient and reliable. Yalkowsky, S. et al. J. Pharm. Studies 87(7): 787-796.

In vivo hemolysis. Hemolysis can be measured in vivo by analysis of either blood or urine at some time after an intravenous injection. The blood level of hemoglobin is a good indicator of hemolysis because intramascular hemolysis increases the concentration of circulating free hemoglobin in the blood. Urine levels of hemoglobin have also been used as an indicator of hemolysis, but they are considered much less reliable than blood levels. Various quantitation methods of measuring intravascular hemolysis are further described in Krzyzaniak et al. Int. J. Pharm. 152: 193-200, 1997 and Krzyzaniak et al. J. Pharm. Sci. 86: 1215-1217 (1997).

In vivo precipitation. Precipitation can be tested for by excising the injecting ear vein and examining it under polarized light. This technique can be used to confirm that, for example, bisantrene precipitates in the rabbit ear vein following an IV injection. Small crystals as well as a bright orange stain, which is characteristic of bisantrene, on the inner wall of the excised vein, are considered indications of precipitation. Powis, G. et al. Cancer Res. 43: 925-929, 1987. Other tests were conducted in monkeys that were given the drug by jugular cannulation. Davio, S. et al. Pharm. Res. 8: 80-83, 1991.

In vivo phlebitis. One of the most often used models for evaluation of phlebitis is the marginal rabbit ear vein, because it is easily viewed and accessible. Most of evaluations of phlebitis are based upon a visual comparison of the injected ear with the noninjected ear, wherein a specified amount of the drug or formulation is injected at a specified rate into one vein, and the same vein on the other ear and the same vein on the other ear is used as a control. Table 1 summarizes a scale for visual evaluation of phlebitis in the rabbit (Ward et al. J. Parenter. Sci. Technol. 47: 40-43, 1993).

TABLE 1

| Rating | Vein color change | Region of edema or erythrema | Inflammation over entire ear |
|---|---|---|---|
| 0 | no | none | no |
| 1 | yes | none | no |
| 2 | yes | 1-3 mm | no |
| 3 | yes | 4-8 mm | no |
| 4 | yes | ≥9 mm | no |
| 5 | yes | diffuse | yes |

Another technique (Ward et al. J. Parenter. Sci. Technol. 47: 161-165, 1993; Ward et al. Pharm. Res. 8:76-79, 1991; Ward et al. Pharm Res. 8: 801-803, 1991; White et al. Pharm. Res. 8: 1340-1341, 1991), utilizes thermal fluctuations in the injected ear for the early detection of phlebitis. Briefly, a specified amount of the drug or formulation is injected at a specified rate into the marginal ear vein of a rabbit, whereas the same vein on the other ear is used as a control to account for normal temperature fluctuations, and both ears are monitored for up to 24 hours after injection. Measuring the temperature increase can be done, for example, by a thermal imaging camera or thermocouples. In this method, a temperature difference of over 2° C. indicates severe phlebitis, an increase of between 1 and 2° C. suggests moderate phlebitis, 0.5-1° C. suggests mild phlebitis, and less than 0.5° C. suggests no phlebitis.

In vivo pain. Assessment of pain in vivo can be performed, for example, as described in Yalkowsky et al. J. Pharm. Studies 87(7):787-796.

In vitro methods. While in vivo studies provide the most direct measure of the problems encountered with intravenous dosing, some in vitro studies can be performed as well, particularly, for early formulation development. For example, assessment of hemolysis and tissue damage in vitro can be assessed as described in Reed et al., J. Parenter. Sci. Technol. 39: 64, 1985; Reed et al. J. Parenter. Sci. Technol. 40: 88, 1986; Reed et al. J. Parenter. Sci. Technol. 41: 37-39, 1987; Obeng et al. J. Parenter. Sci. Technol. 43: 167-173, 1989; Krzyzaniak et al. J. Pharm, Sci. 86: 1215-1217, 1997. Precipitation can be determined in vitro as described in Yalkowsky et al. J. Pharm. Sci. 72: 1014-1017, 1983; Davio et al. Pharm. Res. 8: 80-83, 1991. Phlebitis can be measured as discussed, for example, in Johnson et al. J. Pharm. Sci. 92(8): 1574-1581, 2003.

III. Calcimimetics Compounds

As used herein, the term "calcimimetic compounds" refers to compounds that bind to a calcium receptor, and induce a conformational change that reduces the threshold for calcium receptor activation by the endogenous ligand $Ca^{2+}$, thereby reducing parathyroid hormone ("PTH") secretion. These calcimimetic compounds can also be considered allosteric modulators of the calcium receptor.

Calcimimetic compounds useful in the present invention include those disclosed in, for example, European Patent No. 637,237, 657,029, 724,561, 787,122, 907,631, 933,354, 1,203,761, 1,235,797, 1,258,471, 1,275,635, 1,281,702, 1,284,963, 1,296,142, 1,308,436, 1,509,497, 1,509,518, 1,553,078; International Publication Nos. WO 93/04373, WO 94/18959, WO 95/11221, WO 96/12697, WO 97/41090, WO 01/34562, WO 01/90069, WO 02/14259, WO 02/059102, WO 03/099776, WO 03/099814, WO 04/017908; WO 04/094362, WO 04/106280, WO 06/117211; WO 06/123725; U.S. Pat. Nos. 5,688,938, 5,763,569, 5,962,314, 5,981,599, 6,001,884, 6,011,068, 6,031,003, 6,172,091, 6,211,244, 6,313,146, 6,342,532, 6,362,231, 6,432,656, 6,710,088, 6,750,255, 6,908,935, 7,157,498, 7,176,322 and U.S. Patent Application Publication No. 2002/0107406, 2003/0008876, 2003/0144526, 2003/0176485, 2003/0199497, 2004/0006130, 2004/0077619, 2005/0032796, 2005/0107448, 2005/0143426, European patent application PCT/EP2006/004166, French patent application 0511940.

In one aspect, the invention provides calcimimetic compounds of Formula I and pharmaceutically acceptable salts thereof

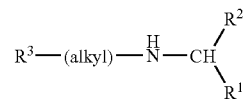

I wherein alkyl is straight or branched-chain $C_1$-$C_8$ alkylene;
$R^1$ is lower alkyl of from 1 to 3 carbon atoms or lower haloalkyl of from 1 to 3 carbon atoms substituted with from 1 to 7 halogen atoms; and $R^2$ and $R^3$ are independently selected monocyclic or bicyclic carbocyclic aryl or cycloalkyl groups, having 5- to 7-membered rings optionally substituted with 1 to 5 substituents each independently selected from the group consisting of lower alkyl of 1 to 3 carbon atoms, lower haloalkyl of 1 to 3 carbon atoms substituted with 1 to 7 halogen atoms, lower alkoxy of 1 to 3 carbon atoms, halogen, nitro, amino, alkylamino, amido, lower alkylamido of 1 to 3 carbon atoms, cyano, hydroxy, acyl of 2 to 4 carbon atoms, lower hydroxylalkyl of 1 to 3 carbon atoms, and lower thioalkyl of 1 to 3 carbon atoms; or a pharmaceutically acceptable salt thereof.

In another aspect, the calcimimetic compound can be chosen from compounds of Formula II and pharmaceutically acceptable salts thereof:

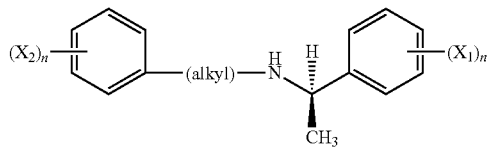

wherein:

$X_1$ and $X_2$, which may be identical or different, are each a radical chosen from $CH_3$, $CH_3O$, $CH_3CH_2O$, Br, Cl, F, $CF_3$, $CHF_2$, $CH_2F$, $CF_3O$, $CH_3S$, OH, $CH_2OH$, $CONH_2$, CN, $NO_2$, $CH_3CH_2$, propyl, isopropyl, butyl, isobutyl, t-butyl, acetoxy, and acetyl radicals, or two of $X_1$ may together form an entity chosen from fused cycloaliphatic rings, fused aromatic rings, and a methylene dioxy radical, or two of $X_2$ may together form an entity chosen from fused cycloaliphatic rings, fused aromatic rings, and a methylene dioxy radical; provided that $X_2$ is not a 3-t-butyl radical;

n ranges from 0 to 5;

m ranges from 1 to 5; and the alkyl radical is chosen from C1-C3 alkyl radicals, which are optionally substituted with at least one group chosen from saturated and unsaturated, linear, branched, and cyclic C1-C9 alkyl groups, dihydroindolyl and thiodihydroindolyl groups, and 2-, 3-, and 4-piperid(in)yl groups.

The calcimimetic compound may also be chosen from compounds of Formula III:

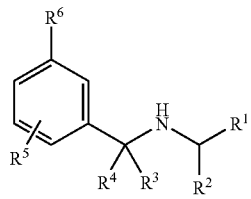

and pharmaceutically acceptable salts thereof, wherein:

$R^1$ is aryl, substituted aryl, heterocyclyl, substituted heterocyclyl, cycloalkyl, or substituted cycloalkyl;

$R^2$ is alkyl or haloalkyl;

$R^3$ is H, alkyl or haloalkyl;

$R^4$ is H, alkyl, or haloalkyl;

each $R^5$ present is independently selected from the group consisting of alkyl, substituted alkyl, alkoxy, substituted alkoxy, halogen, —C(=O)OH, —CN, —$NR^dS(=O)mR^d$, —$NR^dC(=O)NR^aR^d$, —$NR^dS(=O)mR^dR^d$, or —$NR^dC(=O)R^d$;

$R^6$ is aryl, substituted aryl, heterocyclyl, substituted heterocyclyl, cycloalkyl, or substituted cycloalkyl;

each $R^a$ is, independently, H, alkyl or haloalkyl;

each $R^b$ is, independently, aryl, aralkyl, heterocyclyl, or heterocyclylalkyl, each of which may be unsubstituted or substituted by up to 3 substituents selected from the group consisting of alkyl, halogen, haloalkyl, alkoxy, cyano, and nitro;

each $R^c$ is, independently, alkyl, haloalkyl, phenyl or benzyl, each of which may be substituted or unsubstituted;

each $R^d$ is, independently, H, alkyl, aryl, aralkyl, heterocyclyl, or heterocyclylalkyl wherein the alkyl, aryl, aralkyl, heterocyclyl, and heterocyclylalkyl are substituted by 0, 1, 2, 3 or 4 substituents selected from alkyl, halogen, haloalkyl, alkoxy, cyano, nitro, $R^b$, —C(=O)$R^c$, —$OR^b$, —$NR^aR^a$, —$NR^aR^b$, —C(=O)$OR^c$, —C(=O)$NR^aR^a$, —OC(=O)$R^c$, —$NR^aC(=O)R^c$, —$NR^aS(=O)nR^c$ and —S(=O)n$NR^aR^a$;

m is 1 or 2;

n is 0, 1 or 2; and p is 0, 1, 2, 3, or 4;

In one aspect of the invention the compound of Formula III can have the formula

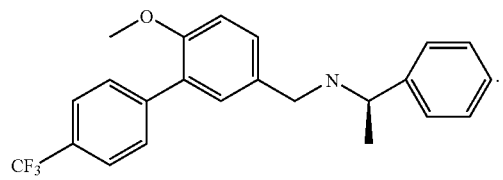

Some of the calcimimetic compounds disclosed herein have the Formula IV

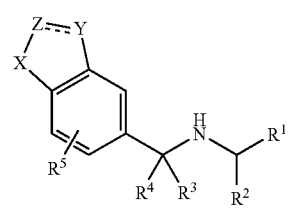

and pharmaceutically acceptable salts thereof, wherein

‑ ‑ ‑ ‑ ‑ represents a double or single bond $R^1$ is $R^1$;

$R^2$ is $C_{1-8}$ alkyl or $C_{1-4}$ haloalkyl;

$R^3$ is H, $C_{1-4}$ haloalkyl or $C_{1-8}$ alkyl;

$R^4$ is H, $C_{1-4}$ haloalkyl or $C_{1-4}$ alkyl $R^5$ is, independently, in each instance, H, $C_{1-8}$alkyl, $C_{1-4}$haloalkyl, halogen, —$OC_{1-6}$alkyl, —$NR^aR^d$ or $NR^dC(=O)R^d$;

X is —$CR^d$=N—, —N=$CR^d$—, O, S or —$NR^d$—;

when ‑ ‑ ‑ ‑ ‑ is a double bond then Y is =$CR^6$— or =N— and Z is —$CR^7$= or —N=; and when ‑ ‑ ‑ ‑ ‑ is a single bond then Y is —$CR^aR^6$— or —$NR^d$— and Z is —$CR^aR^7$— or —$NR^d$—; and $R^6$ is $R^d$, $C_{1-4}$haloalkyl, —C(=O)$R^c$, —$OC_{1-6}$alkyl, —$OR^b$, —$NR^aR^a$, —$NR^aR^b$, —C(=O)$OR^c$, —C(=O)$NR^aR^a$, —OC(=O)$R^c$, —$NR^aC(=O)R^c$, cyano, nitro, —$NR^aS(=O)_mR^c$ or —S(=O)$_mNR^aR^a$;

$R^7$ is $R^d$, $C_{1-4}$haloalkyl, —C(=O)$R^c$, —$OC_{1-6}$alkyl, —$OR^b$, —$NR^aR^a$, —$NR^aR^b$, —C(=O)$OR^c$, —C(=O)

NR$^a$R$^a$, —OC(=O)R$^c$, —NR$^a$C(=O)R$^c$, cyano, nitro, —NR$^a$S(=O)$_m$R$^c$ or —S(=O)$_m$NR$^a$R$^a$;

or R$^6$ and R$^7$ together form a 3- to 6-atom saturated or unsaturated bridge containing 0, 1, 2 or 3 N atoms and 0, 1 or 2 atoms selected from S and O, wherein the bridge is substituted by 0, 1 or 2 substituents selected from R$^5$; wherein when R$^6$ and R$^7$ form a benzo bridge, then the benzo bridge may be additionally substituted by a 3- or 4-atoms bridge containing 1 or 2 atoms selected from N and O, wherein the bridge is substituted by 0 or 1 substituents selected from C$_{1-4}$alkyl;

R$^a$ is, independently, at each instance, H, C$_{1-4}$haloalkyl or C$_{1-6}$alkyl;

R$^b$ is, independently, at each instance, phenyl, benzyl, naphthyl or a saturated or unsaturated 5- or 6-membered ring heterocycle containing 1, 2 or 3 atoms selected from N, O and S, with no more than 2 of the atoms selected from O and S, wherein the phenyl, benzyl or heterocycle are substituted by 0, 1, 2 or 3 substituents selected from C$_{1-6}$alkyl, halogen, C$_{1-4}$haloalkyl, —OC$_{1-6}$alkyl, cyano and nitro;

R$^c$ is, independently, at each instance, C$_{1-6}$alkyl, C$_{1-4}$haloalkyl, phenyl or benzyl;

R$^d$ is, independently, at each instance, H, C$_{1-6}$alkyl, phenyl, benzyl or a saturated or unsaturated 5- or 6-membered ring heterocycle containing 1, 2 or 3 atoms selected from N, O and S, with no more than 2 of the atoms selected from O and S, wherein the C$_{1-6}$ alkyl, phenyl, benzyl, naphthyl and heterocycle are substituted by 0, 1, 2, 3 or 4 substituents selected from C$_{1-6}$alkyl, halogen, C$_{1-4}$haloalkyl, —OC$_{1-6}$alkyl, cyano and nitro, R$^b$, —C(=O)R$^c$, —OR$^b$, —NR$^a$R$^a$, —NR$^a$R$^b$, —C(=O)OR$^c$, —C(=O)NR$^a$R$^a$, —OC(=O)R$^c$, —NR$^a$C(=O)R$^c$, —NR$^a$S(=O)$_m$R$^c$ and —S(=O)$_m$NR$^a$R$^a$; and m is 1 or 2 or a pharmaceutically acceptable salt thereof.

Other examples of calcimimetic compounds described herein have the Formula V:

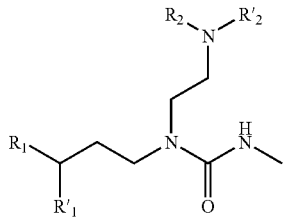

V

R$_1$ and R'$_1$, which may be the same or different, represent an aryl radical, a heteroaryl radical, an aryl or heteroaryl radical substituted by one or more halogen atoms, by one or more hydroxy groups, by one or more linear or branched alkyl or alkoxy radicals containing from 1 to 5 carbon atoms, by one or more trifluoromethyl, trifluoromethoxy, —CN, —NO$_2$, acetyl, carboxyl, carboalkoxy or thioalkyl groups and the oxidised sulfoxide or sulfone forms thereof, thiofluoroalkoxy groups, or R$_1$ and R'$_1$ form, with the carbon atom to which they are linked, a cycle of formula:

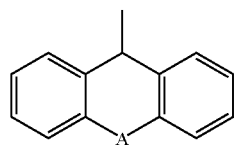

in which A represents a single bond, a —CH$_2$— group, an oxygen, nitrogen or sulfur atom, R$_2$ and R'$_2$ form, with the nitrogen atom to which they are linked, a saturated heterocycle containing 4 or 5 carbon atoms optionally substituted by one or more linear or branched alkyl radicals containing from 1 to 5 carbon atoms, said heterocycle optionally containing a further heteroatom, itself being optionally substituted by a radical R$_5$ in which R$_5$ represents a hydrogen atom, a linear or branched alkyl radical containing from 1 to 5 carbon atoms, optionally substituted by an alkoxy or acyloxy radical, or R$_2$ and R'$_2$, which may be the same or different, represent a hydrogen atom, a linear or branched alkyl radical containing from 1 to 5 carbon atoms optionally substituted by a hydroxy or alkoxy radical containing from 1 to 5 carbon atoms, R$_3$ represents a thiazolyl, oxazolyl, benzothiazolyl or benzoxazolyl group of formula:

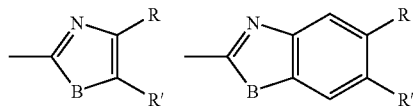

in which B represents an oxygen atom or a sulfur atom, in which R and R', which may be the same or different, represent a hydrogen atom, a halogen atom, a hydroxy radical, a trifluoromethyl radical, a trifluoromethoxy radical, alkyl, alkoxy, alkoxycarbonyl or alkylthio radicals and the oxidised sulfoxide and sulfone form thereof linear or branched containing from 1 to 5 carbon atoms, an aryl or heteroaryl radical, an aryl or heteroaryl radical substituted by one or more groups selected from a halogen atom, a linear or branched alkyl radical containing from 1 to 5 carbon atoms, a trifluoromethyl radical, a trifluoromethoxy radical, a —CN group, an amino, dialkylamino and —NH—CO-alkyl group, an alkylthio group and the oxidised sulfoxide and sulfone form thereof, an alkylsulfonamide —NH—SO$_2$-alkyl group or by a morpholino group, or R and R' on the thiazolyl or oxazolyl group can form a saturated or unsaturated cycle comprising or not comprising one or more optionally substituted heteroatoms, or a pharmaceutically acceptable salt thereof.

Specific examples of calcimimetic compounds of Formula V include is 3-(1,3-benzothiazol-2-yl)-1-(3,3-diphenylpropyl)-1-(2-(4-morpholinyl)ethyl)urea and N-(4-(2-((((3,3-diphenylpropyl)(2-(4-morpholinyl)ethyl)amino)carbonyl)amino)-1,3-thiazol-4-yl)phenyl)methanesulfonamide or pharmaceutically acceptable salt thereof.

Other exemplary calcimimetic compounds fall within Formula VI:

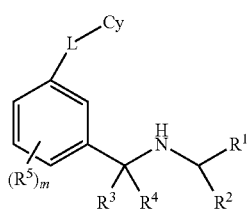

VI wherein:

R$^1$ is phenyl, benzyl, naphthyl or a saturated or unsaturated 5- or 6-membered heterocyclic ring containing 1, 2 or 3 atoms selected from N, O and S, with no more than 2 of the atoms selected from O and S, wherein the phenyl, benzyl, naphthyl or heterocyclic ring are substituted by 0, 1, 2 or 3 substituents selected from C$_{1-6}$alkyl, halogen, C$_{1-4}$haloalkyl, —OC$_{1-6}$ alkyl, cyano and nitro;

$R^2$ is $C_{1-8}$alkyl or $C_{1-4}$haloalkyl;

$R^3$ is H, $C_{1-4}$haloalkyl or $C_{1-8}$alkyl;

$R^4$ is H, $C_{1-4}$haloalkyl or $C_{1-8}$alkyl;

$R^5$ is, independently, in each instance, H, $C_{1-8}$alkyl, $C_{1-4}$haloalkyl, halogen, —$OC_{1-6}$alkyl, —$NR^aR^d$, $NR^aC(=O)R^d$, substituted or unsubstituted pyrrolidinyl, substituted or unsubstituted azetidinyl, or substituted or unsubstituted piperidyl, wherein the substituents can be selected from halogen, —$OR^b$, —$NR^aR^d$, —$C(=O)OR^c$, —$C(=O)NR^aR^d$, —$OC(=O)R^c$, —$NR^aC(=O)R^c$, cyano, nitro, —$NR^aS(=O)_nR^c$ or —$S(=O)_nNR^aR^d$;

L is —O—, —$OC_{1-6}$alkyl-, —$C_{1-6}$alkylO—, —$N(R^a)(R^d)$—, —$NR^aC(=O)$—, —$C(=O)$—, —$C(=O)NR^d$$C_{1-6}$alkyl-, —$C_{1-6}$alkyl-$C(=O)NR^d$—, —$NR^dC(=O)NR^d$—, —$NR^dC(=O)NR^dC_{1-6}$alkyl-, —$NR^aC(=O)R^c$—, —$NR^aC(=O)OR^c$—, —$OC_{1-6}$alkyl-$C(=O)O$—, —$NR^d$$C_{1-6}$alkyl-, —$C_{1-6}$alkyl$NR^d$—, —S—, —$S(=O)_n$—, —$NR^aS(=O)_n$, or —$S(=O)_nN(R^a)$—;

Cy is a partially or fully saturated or unsaturated 5-8 membered monocyclic, 6-12 membered bicyclic, or 7-14 membered tricyclic ring system, the ring system formed of carbon atoms optionally including 1-3 heteroatoms if monocyclic, 1-6 heteroatoms if bicyclic, or 1-9 heteroatoms if tricyclic, and wherein each ring of the ring system is optionally substituted independently with one or more substituents of $R^6$, $C_{1-8}$alkyl, $C_{1-4}$haloalkyl, halogen, cyano, nitro, —$OC_{1-6}$alkyl, —$NR^aR^d$, $NR^dC(=O)R^d$, —$C(=O)OR^c$, —$C(=O)NR^aR^d$, —$OC(=O)R^c$, —$NR^aC(=O)R^c$, —$NR^aS(=O)_mR^c$ or —$S(=O)_mNR^aR^d$;

$R^6$ is a partially or fully saturated or unsaturated 5-8 membered monocyclic, 6-12 membered bicyclic, or 7-14 membered tricyclic ring system, the ring system formed of carbon atoms optionally including 1-3 heteroatoms if monocyclic, 1-6 heteroatoms if bicyclic, or 1-9 heteroatoms if tricyclic, and wherein each ring of the ring system is optionally substituted independently with one or more substituents of $C_{1-8}$alkyl, $C_{1-4}$haloalkyl, halogen, cyano, nitro, —$OC_{1-6}$alkyl, —$NR^aR^d$, $NR^dC(=O)R^d$, —$C(=O)OR^c$, —$C(=O)NR^aR^d$, —$OC(=O)R^c$, —$NR^aC(=O)R^c$, —$NR^aS(=O)_mR^c$ or —$S(=O)_mNR^aR^d$;

$R^a$ is, independently, at each instance, H, $C_{1-4}$haloalkyl, $C_{1-6}$alkyl, $C_{1-6}$alkenyl, $C_{1-6}$alkylaryl or aryl$C_{1-6}$alkyl:

$R^b$ is, independently, at each instance, $C_{1-8}$alkyl, $C_{1-4}$haloalkyl, phenyl, benzyl, naphthyl or a saturated or unsaturated 5- or 6-membered heterocyclic ring containing 1, 2 or 3 atoms selected from N, O and S, with no more than 2 of the atoms selected from O and S, wherein the phenyl, benzyl, naphthyl or heterocyclic ring are substituted by 0, 1, 2 or 3 substituents selected from $C_{1-6}$alkyl, halogen, $C_{1-4}$haloalkyl, —$OC_{1-6}$alkyl, cyano and nitro;

$R^c$ is, independently, at each instance, $C_{1-6}$alkyl, $C_{1-4}$haloalkyl, phenyl or benzyl;

$R^d$ is, independently, at each instance, H, $C_{1-6}$alkyl, $C_{1-6}$alkenyl, phenyl, benzyl, naphthyl or a saturated or unsaturated 5- or 6-membered heterocycle ring containing 1, 2 or 3 atoms selected from N, O and S, with no more than 2 of the atoms selected from O and S, wherein the $C_{1-6}$alkyl, phenyl, benzyl, naphthyl and heterocycle are substituted by 0, 1, 2, 3 or 4 substituents selected from $C_{1-6}$alkyl, halogen, $C_{1-4}$haloalkyl, —$OC_{1-6}$alkyl, cyano and nitro, $R^b$, —$C(=O)R^c$, —$OR^b$, —$NR^aR^b$, —$C(=O)OR^c$, —$C(=O)NR^aR^b$, —$OC(=O)R^c$, —$NR^aC(=O)R^c$, —$NR^aS(=O)_mR^c$ and —$S(=O)_mNR^aR^c$;

m is 1 or 2;

n is 1 or 2;

provided that if L is —O— or —$OC_{1-6}$alkyl-, then Cy is not phenyl;

or a pharmaceutically acceptable salt thereof.

Specific examples of compounds of Formula VI include is N-(2-chloro-5-(((−1-phenylethyl)amino)methyl)phenyl)-5-methyl-3-isoxazolecarboxamide; and N-(2-chloro-5-(((-1-phenylethyl)amino)methyl)phenyl)-2-pyridinecarboxamide, or a pharmaceutically acceptable salt thereof.

In one aspect, a calcimimetic compound is N-(3-[2-chlorophenyl]-propyl)-R-■-methyl-3-methoxybenzylamine HCl. In another aspect, a calcimimetic compound is N-((6-(methyloxy)-4'-(trifluoromethyl)-1,1'-biphenyl-3-yl)methyl)-1-phenylethanamine (Compound A). In another aspect, a calcimimetic compound is (1R)—N-((6-(methyloxy)-4'-((trifluoromethyl)oxy)-1,1'-biphenyl-3-yl)methyl)-1-(1-naphthalenyl)ethanamine (Compound B). In another example, the compound is (1R)—N-((6-(methyloxy)-4'-((trifluoromethyl)oxy)-1,1'-biphenyl-3-yl)methyl)-1-phenylethanamine (Compound C). In still another example, the compound is (1R)-1-(3-fluorophenyl)-N-((6-(methyloxy)-4'-(trifluoromethyl)-1,1'-biphenyl-3-yl)methyl)ethanamine (Compound D). In still another example, the compound is (1R)-1-(3-chlorophenyl)-N-((6-(methyloxy)-4'-(trifluoromethyl)-1,1'-biphenyl-3-yl)methyl)ethanamine (Compound E). In still another example, the compound is (1R)—N-((1-ethyl-3-(3-(trifluoromethyl)phenyl)-1H-indol-5-yl)methyl)-1-phenylethanamine (Compound F). In another example, the compound is (1R)-1-(6-(methyloxy)-4'-(trifluoromethyl)-3-biphenylyl)-N-((1R)-1-phenylethyl)ethanolamine (Compound G). Still another exemplary compound is (1R)—N-((6-chloro-4'-((trifluoromethyl)oxy)-3-biphenyl)methyl)-1-(1-naphthalenyl)ethanolamine (Compound H). While these compounds are noted here as the R enantiomers, it should be understood that the invention contemplates both the R and the S enantiomers and also mixed R/S enantiomer preparations of these compounds. The emulsions of the invention can this be prepared using one, other or both of the R and S enantiomers of these specific compounds as well as other compounds of Formulae I through VI.

Calcimimetic compounds useful in the method of the invention include the calcimimetic compounds described above, as well as their stereoisomers, enantiomers, polymorphs, hydrates, and pharmaceutically acceptable salts of any of the foregoing.

Calcimimetic compounds useful in the present invention can be used in the form of pharmaceutically acceptable salts derived from inorganic or organic acids. The salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, mandelate, methansulfonate, nicotinate, 2-naphthalenesulfonate, oxalate, palmoate, pectinate, persulfate, 2-phenylpropionate, picrate, pivalate, propionate, salicylate, succinate, sulfate, tartrate, thiocyanate, tosylate, mesylate, and undecanoate. When compounds of the invention include an acidic function such as a carboxy group, then suitable pharmaceutically acceptable salts for the carboxy group are well known to those skilled in the art and include, for example, alkaline, alkaline earth, ammonium, quaternary ammonium cations and the like. For additional examples of "pharmacologically acceptable salts," see infra and Berge et al. J. Pharm. Sci. 66: 1, 1977. In certain embodiments the invention salts of hydrochloride and salts of methanesulfonic acid can be used. A skilled artisan would understand that the methods of preparing the formulations of the invention could differ depending on the starting material (e.g., a salt versus free-base). These methods are described in more detail in Examples.

In some aspects of the present invention, the calcium-receptor active compound can be chosen from cinacalcet, i.e., N-(1-(R)-(1-naphthyl)ethyl]-3-[3-(trifluoromethyl)phenyl]-1-aminopropane, cinacalcet HCl, and cinacalcet methanesulfonate. The calcimimetic compound, such as cinacalcet HCl and cinacalcet methanesulfonate, can be in various forms such as amorphous powders, crystalline powders, and mixtures thereof. The crystalline powders can be in forms including polymorphs, psuedopolymorphs, crystal habits, micrometrics, and particle morphology.

The therapeutically effective amount of the calcium receptor-active compound in the compositions disclosed herein ranges from about 1 mg to about 360 mg, for example from about 5 mg to about 240 mg, or from about 20 mg to about 100 mg of the calcimimetic compound per subject. In some aspects, the therapeutically effective amount of cinacalcet HCl or other calcimimetic compound in the composition can be chosen from about 5 mg, about 15 mg, about 20 mg, about 30 mg, about 50 mg, about 60 mg, about 75 mg, about 90 mg, about 120 mg, about 150 mg, about 180 mg, about 210 mg, about 240 mg, about 300 mg, or about 360 mg.

While it may be possible to administer a calcimimetic compound to a subject alone, the compound administered will normally be present as an active ingredient in a pharmaceutical composition. Thus, a pharmaceutical composition of the invention may comprise a therapeutically effective amount of at least one calcimimetic compound, or an effective dosage amount of at least one calcimimetic compound.

As used herein, an "effective dosage amount" is an amount that provides a therapeutically effective amount of the calcimimetic compound when provided as a single dose, in multiple doses, or as a partial dose. Thus, an effective dosage amount of a calcimimetic compound includes an amount less than, equal to or greater than an effective amount of the compound; for example, a pharmaceutical composition in which two or more unit dosages, are required to administer an effective amount of the compound, or alternatively, a multi-dose pharmaceutical composition, in which an effective amount of the calcimimetic compound is administered by administering a portion of the composition. A person skilled in the art would understand that an effective dosage amount of a calcimimetic compound would also depend on whether the formulations of the invention are administered by bolus or by infusion.

IV. Treatment of Disorders

In certain aspects of the present invention, it is contemplated that the emulsion compositions of the present invention may be administered either by itself or in combination with one or more other therapeutic agent(s) that is(are) useful in the treatment of the disorder being treated by a calcimimetic.

In one aspect, the compositions of the invention can be administered for the treatment of hyperparathyroidism (HPT). In one aspect, HPT is secondary HPT. In another aspect, HPT is primary HPT. In a further aspect, the compositions of the invention can be used for treatment of hypercalcemia.

For treatment of HPT, the calcimimetic compounds such as those described herein may be administered in combination with vitamin D, vitamin D-related analogs and steroids, calcium blockers, and the like. Vitamin D is a generic term for a family of secosteroids that have affinity for the vitamin D receptor, and are involved in the physiologic regulation of calcium and phosphate metabolism. See Harrison's Principles of Internal Medicine: Part Eleven, "Disorders of Bone and Mineral Metabolism," E. Braunwald et al., (eds.), 1987, McGraw-Hill, New York at Chapter 335, pp. 1860-1865, Stumpf et al., 1979, Science 206:1188-90, and Holick, 1995, Bone 17:107S-11S. Vitamin D exhibits a complex set of actions and mechanisms of synthesis. Cholecalciferol (vitamin D3) is synthesized in the skin following ultraviolet radiation from 7-dehydrocholesterol. Vitamin D2, an analog of vitamin D3, can be ingested from the diet. Two sequential hydroxylations of vitamin D2 are necessary for full biological activity. The first hydroxylation, which takes place in the liver, results in the formation of 25-hydroxycholecalciferol, while the second hydroxylation takes place in the kidney and results in the formation of the most potent biological metabolite of vitamin D: 1α,25-dihydroxycholecalciferol (also known as calcitriol).

Typically, the active vitamin D compound may be administered, for example, once a week at a dose of at least 0.12 µg/kg per day (8.4 µg in a 70 kg person). Pharmaceutical compositions may be administered in the form for oral, intravenous, intramuscular, topical, transdermal, sublingual, intranasal, intratumoral, or other preparations. Such compositions may comprise 5-100 µg of active vitamin D compound. For further descriptions of compositions comprising vitamin D steroids those of skill in the art are referred to U.S. Patent Application No. 20050101576.

Some exemplary calcimimetic compounds that may be administered in combination with those described herein include, e.g., the calcimimetic agents disclosed in U.S. Pat. Nos. 5,688,938, 5,763,569, 5,858,684, 5,962,314, 6,001,884, 6,011,068, 6,031,003, 6,211,244, 6,313,146, 6,908,935; and 7,176,322, AU 1,400,801 and WO 01/34562 still additional compounds are described herein under the section "calcimimetic compounds". In those embodiments in which the calcimimetic is used for the treatment of hypercalcemia in patients with parathyroid carcinoma, the calcimimetic-containing emulsion may be administered in combination with any antineoplastic intervention that is used for the treatment of carcinoma. Antineoplastic intervention includes but is not limited to radiotherapy, chemotherapy and even surgical resection of the parathyroid gland. Traditional antineoplastic agents include gemcitabine, paclitaxel (Taxol®), 5-Fluorourcil (5-FU), cyclophosphamide (Cytoxan®), temozolomide, or Vincristine. Antineoplastic agents typically fall into a number of subclasses of agents, namely, alkylating agents, antimetabolites, natural products and their derivatives, hormones and steroids (including synthetic analogs), and synthetics. Examples of compounds within these classes are given below.

Exemplary alkylating agents (including nitrogen mustards, ethylenimine derivatives, alkyl sulfonates, nitrosoureas and triazenes) for use in combination with the calcimimetic compostions described herein include Uracil mustard, Chlormethine, Cyclophosphamide (Cytoxan®), Ifosfamide, Melphalan, Chlorambucil, Pipobroman, Triethylene-melamine, Triethylenethiophosphoramine, Busulfan, Carmustine, Lomustine, Streptozocin, Dacarbazine, and Temozolomide. Antimetabolites, e.g., folic acid antagonists, pyrimidine analogs, purine analogs and adenosine deaminase inhibitors, that may be useful include Methotrexate, 5-Fluorouracil, Floxuridine, Cytarabine, 6-Mercaptopurine, 6-Thioguanine, Fludarabine phosphate, Pentostatine, and Gemcitabine. Other chemotherapeutic agents that may be used include the vinca alkaloids, antitumor antibiotics, enzymes, lymphokines and epipodophyllotoxins that are exemplified by compounds such as Vinblastine, Vincristine, Vindesine, Bleomycin, Dactinomycin, Daunorubicin, Doxorubicin, Epirubicin, Idarubicin, paclitaxel (paclitaxel is commercially available as Taxol®), Mithramycin, Deoxyco-formycin, Mitomycin-C, L-Asparaginase, Interferons (especially IFN-α), Etoposide, and Teniposide.

The combination therapy also may be with hormones and steroids such as 17α-Ethinylestradiol, Diethylstilbestrol, Testosterone, Prednisone, Fluoxymesterone, Dromostanolone propionate, Testolactone, Megestrolacetate, Tamoxifen, Methylprednisolone, Methyl-testosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, and Zoladex. Other agents that could be used include Cisplatin, Carboplatin, Hydroxyurea, Amsacrine, Procarbazine, Mitotane, Mitoxantrone, Levamisole, and Hexamethylmelamine.

Methods for administering chemotherapeutic agents are known to those skilled in the art. In addition, their administration is described in the standard literature. For example, the administration of many of the chemotherapeutic agents is described in the "Physicians' Desk Reference" (PDR), e.g., 2006 edition (Medical Economics Company, Montvale, N.J. 07645-1742, USA); the disclosure of which is incorporated herein by reference thereto.

In addition to treatment with an additional therapeutic agent may be one which increases the effectiveness of the calcimimetic. For example, it is known that Sensipar® is metabolized by cytochrome P450 2D6. Co-administration of the cinacalcet-containing emulsions with an agent that inhibits the activity of cytochrome P450 2D6 may be useful in increasing the efficacy of the calcimimetic. Exemplary inhibitory agents include e.g., ketoconazole, erythromycin, itraconazole, fluconazole and the like. Co-administration of the calcimimetic-containing emulsion with a cytochrome P450 2D6 inhibitor will allow a lower dosage of the calcimimetic to be therapeutically effective as compared to a dosage of the calcimimetic e.g., Sensipar® that is administered in the absence of an inhibitor of cytochrome P450 2D6. During such co-administration, serum calcium levels can be monitored to optimize the dosage of the calcimimetic.

In addition to HPT, carcinoma or other hypercalcemia-related disorders discussed above, it is contemplated that the compositions of the invention also may be used in the treatment of a variety of other disorders. Kidney related disorders may be particularly well-suited for therapeutic intervention with the calcimimetic-containing emulsion compositions of the invention. In certain embodiments, the compositions of the invention may be useful in the treatment or prevention of podocyte dysfunction. For example, it is contemplated that the calcimimetic-containing emulsion compositions may be used for treating a podocyte-related disease or disorder. In some embodiments, the podocyte-related disease is podocytopenia. In another aspect, the disease or disorder can manifest in an increase in the foot process width. In a further aspect, the podocyte-related disease or disorder can manifest as effacement or a decrease in slit diaphragm length. In another aspect, the podocyte-related disease or disorder can be a diminution of podocyte density. The podocyte-related disease may have resulted from a podocyte injury caused by, for example, mechanical stress, ischemia, lack of oxygen supply, a toxic substance, an endocrinologic disorder, an infection, a contrast agent, a mechanical trauma, a cytotoxic agent, a medication, an inflammation, radiation, an infection, a dysfunction of the immune system, a genetic disorder, an organ failure, an organ transplantation, or uropathy. In other aspects, the podocyte-related disease or disorder can be due to an abnormal expression or function of nephrin, podocin, FAT-1, CD2AP, Neph1, integrins, integrin-linked kinase, secreted protein acid rich in cysteine, Rho GTPases, -actinin-4, synaptopodin, cyclin-dependent kinase5, podocalyxin, hic-5, GLEPP, TRPC6, dendrin, desmin, snail, notch, synaptopodin, HSP27, lamb4, podocalyxin, NHERF2, Ezrin, dystroglycans, 3 1 integrin collagen type 4 or Wnt-4. In another aspect, the podocyte related disease or disorder can be proteinuria, such as for example, microalbumiuria or macroalbumiuria. In a further aspect, the podocyte disease can be tubular atrophy.

Another kidney-related disorder that may be treated with the compositions of the present invention is polycystic kidney disease.

In still further embodiments, the calcimimetic-containing emulsion compositions of the invention may be used for the treatment of vascular calcification. Vascular calcification is an important and potentially serious complication of chronic renal failure. Two distinct patterns of vascular calcification have been identified (Proudfoot, D & Shanahan, C. Herz 26: 245-51, 2001), and it is common for both types to be present in uremic patients (Chen, N. & Moe, S. Semin Nephrol 24: 61-8, 2004). The first, medial calcification, occurs in the media of the vessel in conjunction with a phenotypic transformation of smooth muscle cells into osteoblast-like cells, while the other, atherogenesis, is associated with lipid-laden macrophages and intimal hyperplasia. Incorporated herein by reference in its entirety is U.S. Patent Application Publication No. 2006276534. The aforementioned application provides exemplification of methods of detection and monitoring of various types of vascular calcification. Such methods may readily be used with the present invention to test for the efficacy and use of the calcimimetic-containing emulsion compositions in treating vascular calcification. In exemplary embodiments, the compositions of the present invention may be used to treat medial wall calcification, atherosclerotic calcification, occlusive arterial disease (also referred to as calciphylaxis or calcific uremic arteriolopathy). "Vascular calcification," as used herein, means formation, growth or deposition of extracellular matrix hydroxyapatite (calcium phosphate) crystal deposits in blood vessels. Vascular calcification encompasses coronary, valvular, aortic, and other blood vessel calcification. The term includes atherosclerotic and medial wall calcification.

In the treatment of vascular calcification, the calcimimetic-containing emulsion compositions may be combined with any agent typically used for the therapeutic intervention of vascular calcification. Such agents include, but are not limited to, multiple calcimimetics, including for example various polymorphs of cinacalcet. For example, calcimimetic compounds that could be used include, but are not limited to those disclosed in, for example, European Patent No. 933 354 and 1 235 797; International Publication Nos. WO 01/34562, WO 93/04373, WO 94/18959, WO 95/11221, WO 96/12697, WO 97/41090; U.S. Pat. Nos. 5,688,938, 5,763,569, 5,962,314, 5,981,599, 6,001,884, 6,011,068, 6,031,003, 6,172,091, 6,211,244, 6,313,146, 6,342,532, 6,362,231, 6,432,656, 6,710,088, 6,908,935 and U.S. Patent Application Publication No. 2002/0107406 (each incorporated herein by reference), other calcimimetic formulae are described herein, e.g., in Formulae I-VI. Additional compounds for use with cinacalcet polymorphs and other calcimimetic-containing emulsions include, for example, vitamin D sterols and/or RENAGEL®.

In still additional embodiments, the compositions of the invention may be used to treat or prevent inflammatory bowel disease, irritable bowel syndrome and other bowel disorders such as, for example, lymphocytic colitis, collagenous colitis, diversion colitis, endometriosis, caustic enema-induced colitis, drug-induced ischemic colitis, NSAID-induced ulcers, nonspecific ulcers, stercoral ulcer, solitary rectal ulcer, typhilitis, colitis cystica profunda, pneumatosis cystoides intestinalis, and malakoplakia.

In the treatment of bowel-related disorders, the calcimimetic-containing emulsions may be combined with one or more other agents used for the treatment of such bowel disease. For example, for patients with constipation-predominant IBS, osmotic laxatives can be used to effect defecation. These laxatives include hypertonic salt solution such as milk of magnesia, poorly absorbable sugars such as lactulose and sorbitol, and isotonic electrolyte solutions containing polyethylene glycol. For diarrhea-predominant IBS, opiate-based agents can be used, such as loperamide, Imodium, bile acid-sequestering drugs, acid-suppressing drugs in the H2 receptor agonist and proton pump inhibitor classes. For pain-predominant IBS, methods of the invention can be practiced together with co-administration of anti-spasmodic agents, such as drugs that block cholinergic nerve function (e.g., dicyclomine, prifinium, cimetropiuim, zamifenacin), agents that prevent calcium flux (e.g., dilatiazem, pinaverium, octylonium, peppermint oil), and direct gut smooth muscle relaxants, as well as agents that act via unknown pathways. Other antispasmodics include mebeverine and trimebutine. In another aspect, calcimimetic-containing emulsion compositions of the invention can be used in the treatment of IBS with antidepressant agents, for example, agents in the tricyclic class, such as amitriotyline, trimipramine, desipramine, nortriotyline, fluphenazine; the selective serotonin reuptake inhibitors, e.g., paroxetine, citalopram, mianserin; or serotonin receptor antagonists, e.g., ondansertron, granisetron, alosertron, or 5HT4 receptor antagonist SB-207266-A.

In yet another embodiment, the calcimimetic-containing emulsion compositions may be used for treating bowel disease in conjunction with other medications, for example, prokinetic medications, such as tegaserod, peripheral dopamine receptor antagonists, such as domperidone; hormonal treatments (for example, gonadotropin-releasing hormone, such as leuprolide; tranquilizers, such as phenaglycodol, meprobamate, heteronium plus amobarbital, propantheline plus phenobarbital, chlordiazepoxide, diazepam, medazepam, and alprazolam. In another aspect, the invention provides methods for treating bowel disease in conjunction with other medications, such as agents that blunt visceral hyperalgesia in bowel disease, for example, kappa-opioid compounds, α2-adrenoceptor agonists (e.g., yohimbine, lidamidine), neurokinin-1 (NK1) receptor antagonists, somatostatin analogs (e.g., octreotide), or oxytocin. In a further aspect, methods of the invention can be practiced in conjunction with psychological therapy, cognitive therapy, biofeedback and stress reduction techniques, and hypnosis. In one aspect, compounds and compositions of the invention can be used in conjunction with itopride, saredutant, renzapride, lubiprostone, or dynogen.

The calcimimetic-containing emulsion compositions of the invention also may be used in treating disorders of intestinal fluid balance, secretion and absorption. In this regard, incorporated herein by reference in its entirety is PCT Publication No. WO 2007/027548, which provides a teaching of methods for modulating intestinal fluid balance. In specific embodiments, the calcimimetic-containing emulsion compositions of the invention may be used in the treatment of diarrhea or other disorders that manifest as an abnormal intestinal motility. The diarrhea may be an osmotic, secretory, exudative or rapid transit diarrhea. It may be acute or chronic. It may be caused by exposure to one or more of a variety of infective agents (e.g., *E. coli, Shigella, Salmonella, Campylobacter jejuni, Vibrio cholera*, cholera toxin, El tor, Giardiasis, *Entamoeba histolyca, cryptosporidium parvum*, Norfolk viruses, Rotaviruses, Adenoviruses Caliciviruses, Astroviruses or Enteroviruses). The diarrhea may be caused by an alteration in cAMP or cGMP or as a result of exposure to antibiotics, anti-inflammatory agents, caffeine, steroids, drugs, laxatives and the like. The diarrhea also may be caused by malabsorption or maldigestion. In still other embodiments, it may be caused by lactase deficiency or short bowel syndrome. Diarrhea also may be due to gastrointestinal surgery, e.g., abdominal procedure or caused by chemotherapy, radiation treatment, inflammation or toxic traumatic injury.

In any of the combination therapies, be they for the treatment of HPT, carcinoma or other hypercalcemia-related disorder, the emulsions may be administered concurrently or sequentially with the second agent with which it is being combined.

The method of treatment will comprise administering to a patient in need thereof, concurrently or sequentially, a therapeutically effective amount of (a) at least the emulsion disclosed herein, and (b) the second therapeutic agent with which the patient is being treated. For example, for the treatment of carcinoma, the second therapeutic agent will be an antineoplastic agent as discussed above. Where the condition being treated is HPT, the second therapeutic agent may be e.g., vitamin D, a calcium binding agent or the like.

The amount and frequency of administration of the emulsion of the invention and the second therapeutic agent (e.g., chemotherapeutic agents and/or radiation therapy and/or other agent for treating hypercalcemia) will be regulated according to the judgment of the attending clinician (physician) considering such factors as age, condition and size of the patient as well as severity of the disease being treated. Intermittent therapy (e.g., one week out of three weeks or three out of four weeks) may also be used.

The second therapeutic agent can be administered according to therapeutic protocols well known in the art. It will be apparent to those skilled in the art that in cancer therapy, the administration of the vitamin D steroid or chemotherapeutic agent and/or radiation therapy can be varied depending on the disease being treated and the known effects of the chemotherapeutic agent and/or radiation therapy on that disease. Also, in accordance with the knowledge of the skilled clinician, the therapeutic protocols (e.g., dosage amounts and times of administration) can be varied in view of the observed effects of the administered therapeutic agents (i.e., antineoplastic agent or radiation) on the patient, and in view of the observed responses of the disease to the administered therapeutic agents.

As noted above, in one of the methods of this invention, the inventive emulsion composition is administered concurrently or sequentially with a second therapeutic agent. Thus, it is not necessary that, for example, the second therapeutic agent and the emulsion composition, should be administered simultaneously or essentially simultaneously.

Furthermore, in general, the inventive emulsion composition and the second therapeutic agent do not have to be administered in the same pharmaceutical composition, and may, because of different physical and chemical characteristics, have to be administered by different routes. For example, the inventive emulsion composition may be administered intravenously to generate and maintain good blood levels thereof, while the other agent may be administered orally. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician.

The particular choice of an emulsion composition/second therapeutic agent combination will depend upon the diagnosis of the attending physicians and their judgment of the condition of the patient and the appropriate treatment protocol.

Where the emulsion composition, and the second therapeutic agent are not administered simultaneously or essentially simultaneously, the order of administration of the emulsion composition, and the second therapeutic agent, may not be important. Thus, the inventive emulsion composition may be administered first, followed by the administration of the second therapeutic agent (e.g., chemotherapeutic agent and/or radiation); or the second therapeutic agent may be administered first, followed by the administration of the emulsion composition. This alternate administration may be repeated during a single treatment protocol. The determination of the order of administration, and the number of repetitions of administration of each therapeutic agent during a treatment protocol, is well within the knowledge of the skilled physician after evaluation of the disease being treated and the condition of the patient.

The practicing physician can modify each protocol for the administration of a component (therapeutic agent—i.e., the inventive emulsion composition, and the second therapeutic agent—e.g., a chemotherapeutic agent or radiation) of the treatment according to the individual patient's needs, as the treatment proceeds. The attending clinician, in judging whether treatment is effective at the dosage administered, will consider the general well-being of the patient as well as more definite signs such as relief of disease-related symptoms, e.g., anxiety, depression, nausea, vomiting, bone fractures, kidney stones as well as monitoring the iPTH, serum calcium levels, serum phosphorus levels, monitoring the subject for adynamic bone disease (e.g., using standard Nichols IRMA). Relief of disease-related symptoms and improvement in overall condition can also be used to help judge effectiveness of treatment.

V. Formulations of the Invention

The present invention provides for drug delivery compositions that are suitable for the intravenous and intra-arterial administration modes of administration. The formulations contain the active agent, generally a therapeutic drug compound, dissolved within the components of the composition. The emulsion formulations are stable, and can thus be stored over a period of time without concomitant loss of active agent activity or drug delivery composition performance. The present invention also provides methods for preparing the drug delivery compositions, and methods for administering the drug delivery compositions to a subject. The emulsions of the present invention are specifically adapted for use with irritant therapeutic agents, such as if the agents are found to be irritants (e.g., capable of causing irritation, pain upon injection, precipitation, phlebitis or hemolysis) when administered intravenously in a solution, by formulating them in the emulsions of the invention, this irritation as determined by in vitro or in vivo tests described above is reduced or eliminated. The irritant agents suitable for use in this invention are either hydrophobic or amphiphilic. The examples of agents useful in the present invention include penicillin, an aminoglycoside, aminocyclitrol, tetracycline, macrolide antibiotics, cephalosporin antibiotics, antimalarials, antiprotozoals, antihelmintics, antineoplastics, benzodiazepines, phenothiazines, anesthetics, skeletal muscle relaxants, antirheumatics, adrenergic agents, peptide drugs, protein drugs, calcimimetics, and nonsteroidal anti-inflammatory agents. The active irritant agent, or drug, can be present in the emulsions in an amount of from about 0.001 to about 5, or from about 0.5 to about 3, or from about 0.5 to about 2.5, percent by weight.

Examples of suitable oils for purposes of this invention include triesters of glycerol with fatty acids having 6 to 14 carbon atoms, and vegetable oils, such as soybean oil, corn oil, poppy seed oil and the like, which are generally liquid at body temperatures, and mixtures thereof. The triglycerides can be defined as short chain triglycerides having 9-15 carbon atoms, medium chain triglycerides having 21-45 carbon atoms, and long chain triglycerides having above 45 carbon atoms. The long chain triglycerides may be further subdivided into saturated, mono-unsaturated and polyunsaturated triglycerides, depending on whether the fatty acyl moieties of the triglyceride contain no, one, or more than one, double carbon-carbon bond. Mono or polyunsaturated long chain triglycerides, short chain and medium chain triglycerides, such as short or medium chain. Examples of oils include the vegetable or the hydrogenated vegetable oil, such as peanut oil, corn oil, castor oil, cottonseed oil, soybean oil, olive oil, safflower oil, peppermint oil, coconut oil and palm seed oil. Other examples include beeswax, vitamin E, oleic acid, medium chain monoglycerides, diglycerides, triglycerides, structured triglycerides, and mixtures thereof. Oil components of the formulation may vary from 1 to 30% by weight.

Examples of suitable phospholipids (a class of lipids formed from four components: fatty acids, a negatively-charged phosphate group, an alcohol and a backbone) include egg lecithin, egg yolk phospholipids, soy lecithin or soybean phospholipids. It can be present in the formulation in an amount from 0.1 to 5% by weight.

The formulations of the invention can also include a charge stabilizer. This can be an acid (such as hydrochloric acid, tartaric acid, benzoic acid, citric acid oleic acid, linoleic acid, stearic acid, palmitic acid, decanoic acid, lauric acid, myristic acid, icosanoic acid, behenic acid, myristoleic acid, palmitoleic acid, alpha linolenic acid, arachidonic acid, and eicosapentanoic acid, salts thereof) or a salt thereof, a base, (for example, KOH or NaOH or any other suitable base) or a buffer, such as diethanolamine, glycine, citrate, acetate, histidine, phosphate, carbonate, meglumine, N-methyl glucamine and tris(hydroxymethyl)aminomethane (TRIS) buffers.

In certain embodiments, the present invention provides kits for administering the emulsion composition of the invention, which kit comprises, in a container, the emulsion composition, instructions and instruments for administration of the emulsion composition. The kit also may optionally comprise one or more additional components, such as for example, additional therapeutic compositions, pharmaceutical carriers or diluents for mixing the emulsion composition prior to administration, assay components for determining the efficacy of the emulsion composition (e.g., assay components for determining the level of iPTH, serum calcium, serum phosphorus and the like), instruments for obtaining serum to test for the efficacy of the emulsion composition and the like.

The following examples are offered to more fully illustrate the invention, but are not to be construed as limiting the scope thereof.

were shaken at room temperature for eighteen hours on a platform shaker. After eighteen hours, the samples were diluted in mobile phase, and analyzed by the RP-HPLC method. Table 2 summarizes solubility results (expressed in mg/mL) of cinacalcet in various oil phases.

TABLE 2

| Lecithin | Medium Chain Triglycerides | Structured Triglycerides | Long Chain Triglycerides |
|---|---|---|---|
| — | >341 | >368 | >340 |
| Egg | >349 | >339 | >362 |
| Soy | >327 | >317 | >304 |

Table 3 summarizes solubility of other calcimimetics in long-chain oil phases.

TABLE 3

| Name | Chemical name | Solubility (mg/mL) |
|---|---|---|
| Compound A | (1R)—N-((6-(methyloxy)-4'-(trifluoromethyl)-1,1'-biphenyl-3-yl)methyl)-1-phenylethanamine | >300 |
| Compound B | (1R)—N-((6-(methyloxy)-4'-((trifluoromethyl)oxy)-1,1'-biphenyl-3-yl)methyl)-1-(1-naphthalenyl)ethanamine | 50 |
| Compound C | (1R)—N-((6-(methyloxy)-4'-((trifluoromethyl)oxy)-1,1'-biphenyl-3-yl)methyl)-1-phenylethanamine | >300 |
| Compound D | (1R)-1-(3-fluorophenyl)-N-((6-(methyloxy)-4'-(trifluoromethyl)-1,1'-biphenyl-3-yl)methyl)ethanamine | >300 |
| Compound E | (1R)-1-(3-chlorophenyl)-N-((6-(methyloxy)-4'-(trifluoromethyl)-1,1'-biphenyl-3-yl)methyl)ethanamine | >300 |
| Compound F | (1R)—N-((1-ethyl-3-(3-(trifluoromethyl)phenyl)-1H-indol-5-yl)methyl)-1-phenylethanamine | >300 |
| Compound G | (1R)-1-(6-(methyloxy)-4'-(trifluoromethyl)-3-biphenylyl)-N—((1R)-1-pheylethyl) ethanolamine | >50 |
| Compound H | (1R)—N-((6-chloro-4'-((trifluoromethyl)oxy)-3-biphenyl)methyl)-1-(1-naphthalenyl) ethanolamine | >50 |

EXAMPLE 1

This example summarizes the solubility data and illustrates the composition of the formulations of the invention.

The solubility measurements of the compounds were prepared by the addition of 1 g of drug substance to two milliliters of oil into a Wheaton 5 mL vial. The headspace was sparged with nitrogen, and enclosed with a West 4405/50 gray Teflon coated stopper and manually sealed by an aluminum overseal. The preparations were repeated again with the oils containing either purified egg or soy lecithin. All labeled vials These results presented above demonstrate that calcimimetic compounds tested have high solubility in different oil phases.

Table 4 illustrates the effect of different oils and phospholipids on pH and particle size of crude emulsions prepared for cinacalcet. The particle size distribution of the droplets was measured using light diffraction techniques after dilution of the emulsion in water. The particle size is represented by D(4,3) which is the volume corrected mean of the particles (units). As used herein, SBO—soybean oil (long chain triglycerides); MCT—medium chain triglycerides; STG—structured triglycerides (including PEGylated oils)

TABLE 4

| | | 1% Purified Egg Lecithin | | 2% Purified Egg Lecithin | | 1% Purified Soy Lecithin | | % Purified Soy Lecithin | |
|---|---|---|---|---|---|---|---|---|---|
| Oil used | % | pH | D(4, 3) | pH | D(4, 3) | pH | D(4, 3) | PH | D(4, 3) |
| SBO | 5 | 8.81 | 1.07 | 8.53 | 0.77 | 8.94 | 1.3 | 8.99 | 0.81 |
| | 10 | 8.80 | 0.65 | 8.46 | 0.68 | 8.86 | 0.98 | 8.91 | 0.4 |
| | 20 | 8.62 | 1.42 | 8.39 | 1.06 | 8.73 | 1.4 | 8.82 | 0.49 |
| MCT | 5 | 8.58 | 0.39 | 8.39 | 0.35 | 9.12 | 0.36 | 8.97 | 0.32 |
| | 10 | 8.61 | 0.53 | 8.29 | 0.40 | 9.09 | 0.21 | 8.99 | 0.44 |
| | 20 | 8.41 | 0.57 | 8.23 | 0.42 | 8.81 | 0.47 | 8.95 | 0.31 |

TABLE 4-continued

|  |  | 1% Purified Egg Lecithin | | 2% Purified Egg Lecithin | | 1% Purified Soy Lecithin | | % Purified Soy Lecithin | |
| --- | --- | --- | --- | --- | --- | --- | --- | --- | --- |
| Oil used | % | pH | D(4,3) | pH | D(4,3) | pH | D(4,3) | PH | D(4,3) |
| STG | 5 | 8.55 | 0.72 | 8.46 | 0.52 | 9.09 | 0.40[a] | 9.04 | 0.34[a] |
|  | 10 | 8.71 | 1.23 | 8.37 | 0.81 | 9.00 | 0.73[a] | 9.01 | 0.41[a] |
|  | 20 | 8.52 | 0.84 | 8.28 | 1.18 | 8.99 | 0.94[a] | 9.07 | 0.46[a] |

[a]Data from emulsions after a single autoclaving cycle

Table 5 summarizes some examples of components of the emulsions of the invention.

TABLE 5

| Component | Example of component | Range |
| --- | --- | --- |
| Drug substance | Calcimimetics | 0.0001-5% w/v |
| Oil phase | Long chain triglycerides | 1-20% w/w |
|  | MCT | 1-20% w/v |
|  | STG | 1-20% w/v |
| Emulsifier | Egg lecithin | 0.1-5% w/w |
|  | Soy Lecithin | 0.1-5% |
| pH range | — | 6-9 |
| Buffer component | TRIS | 1-100 mM |
|  | Diethanolamine amine | 1-100 mM |
| Tonicity adjuster | Glycerol | 0-2.5% w/w |
| Charge Stabilizer | Fatty acids, e.g., oleate, palmitate, stearate etc. | 0-5% w/w |
| Aqueous phase | Water for injection | QS to 100% w/w |

It should be noted that individual integers and fractions of integers between the ranges specified above are specifically contemplated. For example, a range of 0-20% includes 0, 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 10.5%, 11%, 11.5%, 12%, 12.5%, 13%, 13.5% 14%, 14.5%, 15.5%, 16%, 16.5%, 17%, 17.5%, 18%, 18.5%, 19%, 19.5% and 20%. Other components of formulations of the invention, such as additional buffers, stabilizing and tonicity agents are discussed in Examples below.

EXAMPLE 2

This example illustrates different routes of preparation of formulations of the invention.

Materials

Fresenius Kabi supplied the purified egg lecithin, structured triglycerides (STG) and soybean oil, or long chain triglycerides (LCT). Miglyol 810N, or medium chain triglycerides (MCT), was purchased from Condea Chemie (formerly Huls). American Lecithin supplied the soy lecithin. Other common lab chemicals such as sodium hydroxide, Hydrochloric acid, glycerin, isopropyl alcohol, TRIS, diethanolamine etc. were obtained from JT Baker, Sigma chemicals or other suitable vendors.

Coarse prototype emulsion formulations were prepared at a batch size of 10 mLs by an Ultraturrax T25 S1 Janke and Kunkel blade homogenizer equipped with a 10 mm rotostator, followed by sonication from a Vibracell Ultrasonicator with a titanium microtip probe. Batches at a 40 mL size were prepared in a similar manner, with the exception of the ultrasonicator having a ¾" titanium probe tip.

Intermediate manufacture of emulsions at a batch size less than one liter were performed on a Rannie 8.30H MIN-LAB Homogenizer, a two piston high-pressure homogenizer with a flow rate of 167 mL/minute. An UltraTurrax T25 S1 Janke and Kunkel blade homogenizer with a 18 mm rotostator was used to mix the ingredients prior to homogenization. Alternatively, lab scale emulsions with typical batch sizes in the range of 15 mL to 2 liters were prepared using a Sonifer probe sonicator, Ultra Turrex T25 Basic, with appropriate homogenizer probes (IKA Labortechnik) or a Polytron PT 1200C, with appropriate homogenizer probes (Kinematica) to mix the ingredients, with a Microfluidizer, (Microfluidics Inc) used for final homogenization.

Manufacture of emulsions at a batch size of 4-12 liters was performed on a Gaulin M3 Homogenizer, a three piston high-pressure homogenizer with a flow rate of 4.4 L/minute. An Ultra Turrax SD-45 Janke and Kunkel blade homogenizer with a 4,5-cm rotostator was used to mix the ingredients before homogenization.

Manufacture of emulsions at batch size range of 10-100 L was preformed using a homogenization subsystem and passing the emulsion through a high pressure homogenizer at 8000 psi for 8 cycles.

Examples of equipment used for characterization of emulsions included Corning pH meter with an Orion semi-micro Ross electrode or Orion 720 A with Ag/AgCl electrode; Malvern Mastersizer S or Mastersizer 2000 from Malvern Instruments; Zetasizer 4 from Malvern Instruments; Osmette A freezing point osmometer and reverse phase HPLCs.

Methods

Preparation Using Freebase as Starting Material

A. Lab Scale Preparation

Coarse prototype emulsions at a batch size of 10-40 mLs were prepared by mixing the oil with lecithin by a blade mixer at 60° C. protected by a nitrogen headspace. Cinacalcet was added and mixed well, followed by the addition of the aqueous phase containing glycerin and buffer until a homogenous mixture was made. A sonicator probe was used to further process the emulsion premix while maintaining the nitrogen headspace. Coarse emulsions prepared by sonication were centrifuged at 3K RPM to remove gross particulates on a Dupont Sorval centrifuge, and dispensed by removal of the top contents of the emulsion for evaluation.

Fine emulsions prepared by homogenization or microfluidizer followed the following steps.

First, the aqueous phase was prepared by adding appropriate amounts of glycerin, water and buffer to an appropriate container or tank. This was mixed well and maintained at elevated temperatures (60-70° C.) by immersing in an water batch or circulating hot water through outer jacket of the tank.

Next the oil phase was prepared, by adding appropriate oil and lecithin. The container was tared and the drug substance was added. This was mixed at elevated temperature using homogenizer or sonicater probes to disperse lecithin and dissolve the drug substance.

The coarse emulsion was compounded. The hot oil phase was transferred to the aqueous phase at 70° C. and homogenized to obtain coarse emulsion.

Fine emulsion was obtained using a high-pressure homogenizer or microfluidizer. Using a microfluidizer: the emulsion was processed through the microfluidizer at max pressure (>20,000 psi) for a minimum of 5 till a constant particle size was obtained or to a maximum of 12 cycles. The processing chamber of the microfluidizer was covered with ice and to keep the temperature of the emulsion from rising. Using Rannie or Gaulin homogenizer: the emulsion was homogenized for several passes at a pressure of 8000 psi while maintaining nitrogen headspace and the temperature at approximately 50-60° C. pH of the final emulsion was adjusted using 1N HCl or 1N NaOH to achieve the required pH.

Next, the final emulsion was dispensed into pre-cleaned and sterilized glass vials of appropriate capacity. The headspace was purged with nitrogen or other inert gas, the vials were closed with Teflon coated rubber caps and sealed with aluminum overseals.

The emulsions were sterilized by autoclaving.

B. Manufacturing Scale Preparation

FIG. 1 illustrates the manufacturing process flow chart for emulsions of the invention.

First, components were weighed into appropriate vessels as follows. The oil phase, e.g., soybean oil, lecithin and the drug substance were combined, with high-sheer mixing, in the "dissolving vessel". The aqueous phase, e.g., pyrogen-free water, TRIS-base and glycerin were combined, with high-sheer mixing, in the "pre-mix vessel".

Next, each phase was furthermore mixed with a high-sheer mixer. Temperature of each phase was maintained at 50-60° C. The oil phase was transferred, using pressurized nitrogen, into the pre-mix vessel, containing the aqueous phase. The dissolving vessel was rinsed twice with pyrogen-free water, and each rinse was transferred to the pre-mix vessel using pressurized nitrogen. The mixture was adjusted up to the total target weight using pyrogen-free water. The combination was high sheer mixed to form a crude emulsion. After that, the crude emulsion was transferred to "surge tank #1" using nitrogen pressure. Then the crude emulsion was processed through the homogenizer into "surge tank #2" using compressed air to drive the homogenizer. The last two steps can be repeated several times to achieve optimum droplet size.

The optimized emulsion was then transferred to the "filling station" using pressurized nitrogen and filled into vials, which were purged with nitrogen and capped. The emulsion-containing vials were then steam sterilized in a rotational autoclave. All steps in this process were performed under constant nitrogen production.

Preparation Using Salt as Starting Material

A. Sequential Process

For conversion of cinacalcet salt to freebase, cinacalcet HCl was added to an empty jacketed reactor set for 70° C., and the appropriate amount of water was added for irrigation. The reaction was mixed at to form a slurry and the mixing continued to allow the temperature of the slurry to reach 70° C. Next, NaOH solution was added in the amount is approximately 1.1 to 1.2 molar equivalents of the salt, and the mixing continued for 1 hour. The temperature of the re-circulating water was then set to 25° C. and ice added to quickly cool it down to the required temperature.

To extract cinacalcet freebase in soybean oil, the oil was added to the mix by weight, in the amount half the quantity required for final emulsion. The mixture was then stirred at 500 RPM for 2 hours. After that, the stirring was stopped and the mixture was allowed to stand undisturbed for 1 hour. Then the water phase was drained from the bottom outlet of the reactor vessel till most of the water has been removed. The rate of draining was slowed down to drop-wise. The water phase was collected until the oil phase was seen eluting from the outlet. A few drops of oil were allowed to drain out to ensure that no water remains in the reactor. The remainder of the oil phase was collected in a separate tared container and its actual weight was noted. Samples from the oil phase were taken and analyzed as in-process samples.

To prepare an emulsion, the lecithin was dispersed in the second half of the oil required at elevated temperature and the drug-oil solution was added. The emulsion was prepared as described in preparation using freebase above.

B. One-Pot Process

For this process, the salt form of cinacalcet was added to the reaction vessel or tank; hot water was circulated through the jacket to obtain the final temperature of 60-70° C. A small portion of the water required to make to final emulsion was added, and the reaction was mixed well to form a slurry. The mixing continued until final temperature of the slurry reached 60-70° C. A weighted quantity of TRIS base was added and the mixing continued to achieve complete conversion of salt to freebase. To extract the free base form of the drug into the oil phase, soybean oil was added. Then lecithin was added to the same vessel and mixed in the oil. The remaining amount of water was added with glycerin and the NaOH solution was then added to get the desired pH. The reaction was mixed/homogenized to get coarse emulsion, followed by high-pressure homogenization or microfluidization as described above to obtain the final emulsion.

EXAMPLE 3

This Example illustrates the effect of pH and buffer type on the stability of the formulations of the invention as measured by the size and charge of the droplets.

Figure 2:
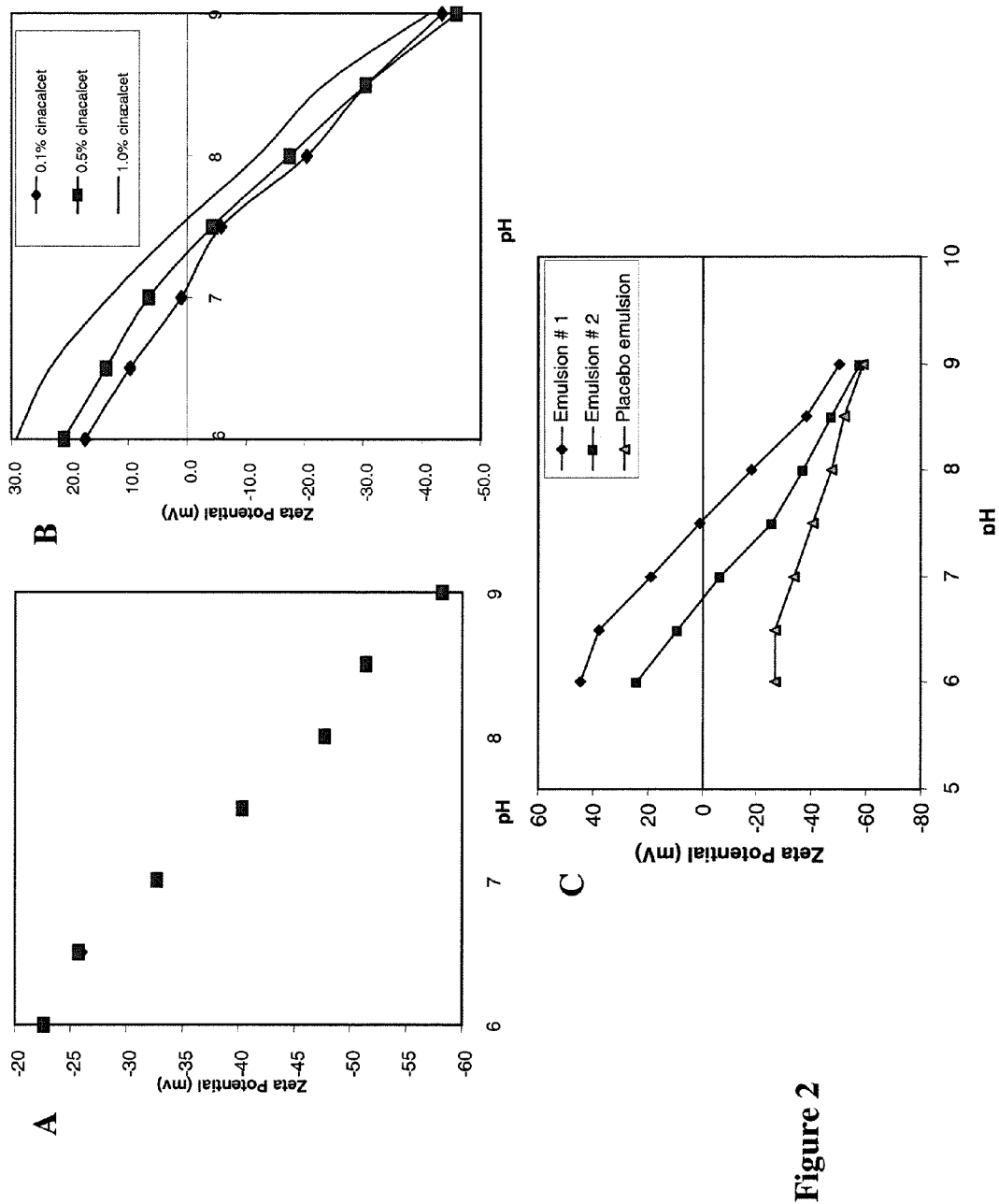
FIG. 2 demonstrates the effect of pH and the presence of a calcimimetic compound on the droplet charge.

The results of these studies are depicted in FIG. 2 which demonstrates the effect of pH and the presence of a calcimimetic compound on the droplet charge. Panel A, titration results of 1% EYP/10% SBO in 1 mM dibasic phosphate. Panel B, titration results of cinacalcet/1% EYP/10% SBO in 1 mM dibasic phosphate. Other components of the emulsions include 10% soybean oil, 1% egg lecithin, 2.25% glycerin and water. Panel C, titration results for Compound A. Emulsion composition: SBO 10%, Lecithin 2% at pH 7. Concentration of Compound A was 5 mg/mL for formulation #1 and 1 mg/mL for formulation #2. The emulsion with higher Compound A concentration reaches neutral charge at a higher pH than that with a lower concentration.

The zeta potential measurements were made on a Malvern Zetasizer 4 laser-scattering particle electrophoretic analyzer that measures the electrophoretic mobility and zeta potential distribution. Samples were prepared for the zeta potential titration by diluting the emulsion approximately 2500 fold in 1 mM dibasic phosphate pH 9 and titrating the solution with 100 mM phosphoric acid in 0.5 pH unit increments. At pH of about 9, both the placebo emulsions and the cinacalcet emulsion carry a net negative charge (FIG. 2). Theoretically, the emulsions are stabilized by this charge, which prevents the droplets from coalescing. As pH is reduced, for the placebo emulsion although the magnitude of the charge is reduced, overall the net negative charge is maintained. In contrast, the cinacalcet emulsions achieve charge neutrality in the range of pH 7-7.5.

Tables 6 summarizes the effect of pH and the buffer type on emulsion stability as measured by the particle size. Emulsions were made using 2% egg lecithin, 2.25% glycerin in water for injection. Particle size and pH were measured after one-autoclave cycle. For all emulsions, particle size before autoclaving as represented by D(4,3) was in a range of 0.30 to 0.45 μm. Emulsions were stable at high pH using TRIS and DEA buffer, and at low pH using phosphate buffer over varying concentrations of cinacalcet and soybean oil. Closer to pH 7 using phosphate buffer, increase in particle size was seen after autoclaving.

TABLE 6

| Buffer | Buffer conc. | Target cinacalcet conc.[a] (mg/mL) | SBO conc. | pH | D(4, 3) μm |
|---|---|---|---|---|---|
| TRIS | 5 mM | 1 | 10 | 8.75 | 0.48 |
|  | 5 mM | 5 | 5 | 8.80 | 0.31 |
|  | 5 mM | 10 | 10 | 8.82 | 0.39 |
|  | 5 mM | 5 | 10 | 8.87 | 0.32 |
|  | 5 mM | 10 | 20 | 8.82 | 0.36 |
|  | 10 mM | 5 | 5 | 9.06 | 0.30 |
|  | 15 mM | 5 | 5 | 9.04 | 0.34 |
|  | 20 mM | 5 | 5 | 9.13 | 0.29 |
| DEA | 0.05% | 1 | 10 | 8.81 | 0.44 |
|  | 0.05% | 5 | 5 | 8.77 | 0.39 |
|  | 0.05% | 10 | 10 | 8.82 | 0.41 |
|  | 0.1% | 5 | 5 | 8.95 | 0.40 |
|  | 0.2% | 5 | 5 | 9.13 | 0.35 |
|  | 0.3% | 5 | 5 | 9.12 | 0.36 |
| PO4 buffer | 10 mM | 5 | 5 | 6.36 | 0.39 |
|  | 10 mM | 5 | 5 | 6.78 | 0.76 |
|  | 15 mM | 5 | 10 | 7.15 | 1.59 |
| No buffer | — | 5 | 10 | 8.45 | 1.48 |

[a]Actual concentration varied by ±10%

Data for emulsions prepared for Compound A using a wide range of excipient levels are summarized in Table 7. Particle size data is reported as D(4,3) before and after one autoclaving cycle.

TABLE 7

| Emulsion # | Compound A mg/ml | SBO % w/w | Egg lecithin % w/w | D:pH | Final pH post autoclave | D(4,3) pre-autoclave | D(4,3) ppst-autoclave |
|---|---|---|---|---|---|---|---|
| 1 | 5 | 10 | 2 | 9 | 9.02 | 0.33 | 0.33 |
| 2 | 5 | 10 | 2 | 7 | 7.14 | 0.24 | 0.65 |
| 3 | 5 | 1 | 0.2 | 7 | 7.19 | 0.36 | 0.71 |
| 4 | 0.5 | 10 | 0.2 | 9 | 9.15 | 0.37 | 0.37 |
| 5 | 0.5 | 5 | 2 | 9 | 9.06 | 0.22 | 0.22 |
| 6 | 0.5 | 1 | 0.4 | 7 | 7.17 | 0.27 | 0.34 |
| 7 | 0.5 | 10 | 2 | 7 | 6.92 | 0.36 | 1.89 |
| 8 | 5 | 10 | 0.2 | 9 | 9.08 | 0.39 | 0.39 |
| 9 | 2.75 | 5.2 | 1.48 | 8.5 | 8.63 | 0.23 | 0.30 |
| 10 | 0.5 | 10 | 2 | 7 | 7.14 | 0.67 | 4.00 |
| 11 | 5 | 7.5 | 2 | 9 | 9.16 | 0.22 | 0.23 |
| 12 | 2.75 | 10 | 2 | 9 | 9.17 | 0.23 | 0.23 |
| 13 | 2.75 | 1 | 0.2 | 9 | 9.38 | 0.26 | 0.25 |
| 14 | 0.5 | 5.4 | 0.96 | 8 | 8.26 | 0.23 | 0.34 |
| 15 | 0.5 | 5.5 | 0.2 | 7 | 7.17 | 1.74 | 41.40 |
| 16 | 2.75 | 5.5 | 0.2 | 8 | 8.10 | 0.69 | 1.42 |
| 17 | 2.75 | 10 | 0.2 | 7 | 7.14 | 1.23 | 1.96 |
| 18 | 0.5 | 5 | 2 | 9 | 8.98 | 0.22 | 0.22 |
| 19 | 2.75 | 5 | 2 | 7 | 7.03 | 0.32 | 0.22 |
| 20 | 3.88 | 7.7 | 1.03 | 7.5 | 7.55 | 0.29 | 0.68 |
| 21 | 2.75 | 10 | 0.2 | 7 | 7.02 | 1.09 | 2.11 |
| 22 | 5 | 10 | 0.2 | 9 | 8.88 | 0.39 | 0.37 |
| 23 | 5 | 3 | 1.2 | 9 | 8.77 | 0.25 | 0.26 |
| 24 | 5 | 5 | 2 | 8 | 8.00 | 0.43 | — |
| 25 | 0.5 | 10 | 0.2 | 9 | 9.00 | 0.37 | 1.38 |
| 26 | 5 | 3 | 1.2 | 7 | 7.04 | 0.21 | 0.24 |
| 27 | 5 | 10 | 0.2 | 9 | 8.90 | 0.36 | 0.40 |
| 28 | 0.5 | 10 | 0.2 | 9 | 8.81 | 0.38 | 0.34 |

EXAMPLE 4

This Example illustrates the effect of the storage temperature on short-term stability of the formulations of the invention as measured by pH and the size of the droplets. The results of short term stability of cinacalcet at different temperatures and varying TRIS buffer concentrations are presented in Table 8. Cinacalcet was stable in the emulsion formulation over 12 weeks. The pH of the emulsion is lower over time for both placebo and cinacalcet emulsions. The drop in pH is less at lower storage temperature and higher TRIS concentration.

TABLE 8

| Storage conditions | | 5° C. | | | 40° C. | | |
|---|---|---|---|---|---|---|---|
| Buffer conc. | Time (weeks) | Cinacalcet conc. mg/mL | pH | D(4, 3) | Cinacalcet conc. mg/mL | pH | D(4, 3) |
| 5 mM | 0 | 0 (placebo) | 8.85 | 0.35 | 0 (placebo) | 8.85 | 0.35 |
| | 2 | 0 (placebo) | 8.75 | 0.35 | 0 (placebo) | 8.59 | 0.33 |
| | 4 | 0 (placebo) | 8.64 | 0.34 | 0 (placebo) | 8.32 | 0.38 |
| | 6 | 0 (placebo) | 8.64 | 0.35 | 0 (placebo) | 8.38 | 0.35 |
| | 8 | 0 (placebo) | 8.74 | 0.35 | 0 (placebo) | 8.19 | 0.35 |
| | 12 | 0 (placebo) | 8.43 | 0.34 | 0 (placebo) | 8.15 | 0.34 |
| | 0 | 4.43 | 8.80 | 0.31 | 4.43 | 8.80 | 0.31 |
| | 2 | 4.18 | 8.69 | 0.31 | 4.17 | 8.41 | 0.31 |
| | 4 | 4.38 | 8.65 | 0.30 | 4.36 | 8.29 | 0.31 |
| | 6 | 4.33 | 8.59 | 0.30 | 4.29 | 8.20 | 0.47 |
| | 8 | 4.47 | 8.60 | 0.31 | 4.45 | 8.11 | 0.48 |
| | 12 | 4.32 | 8.50 | 0.31 | 4.33 | 8.12 | 0.36 |
| 20 mM | 0 | 0 (placebo) | 9.14 | 0.38 | 0 | 9.14 | 0.38 |
| | 2 | 0 (placebo) | 9.03 | 0.39 | 0 | 8.86 | 0.39 |
| | 4 | 0 (placebo) | 8.99 | 0.37 | 0 | 8.76 | 0.37 |
| | 6 | 0 (placebo) | 9.03 | 0.36 | 0 | 8.69 | 0.37 |
| | 8 | 0 (placebo) | 9.03 | 0.38 | 0 | 8.73 | 0.38 |
| | 12 | 0 (placebo) | 8.98 | 0.37 | 0 | 8.61 | 0.38 |
| | 0 | 4.92 | 9.13 | 0.29 | 4.92 | 9.13 | 0.29 |
| | 2 | 4.47 | 8.98 | 0.29 | 4.48 | 8.82 | 0.29 |
| | 4 | 4.79 | 8.99 | 0.29 | 4.75 | 8.79 | 0.29 |
| | 6 | 4.72 | 8.87 | 0.28 | 4.73 | 8.75 | 0.29 |
| | 8 | 4.91 | 9.02 | 0.29 | 4.96 | 8.76 | 0.29 |
| | 12 | 4.76 | 8.93 | 0.29 | 4.82 | 8.63 | 0.29 |

The results of short-term stability of cinacalcet at different temperatures and varying DEA buffer concentrations are presented in Table 9. Cinacalcet was stable in the emulsion formulation over 12 weeks. pH of the emulsion is lower over time for both placebo and cinacalcet emulsion. The drop in pH is less at lower storage temperature and higher DEA concentration.

TABLE 9

| Storage conditions | | 5° C. | | | 40° C. | | |
|---|---|---|---|---|---|---|---|
| Buffer conc. | Time (weeks) | Cinacalcet conc. mg/mL | pH | D(4, 3) | Cinacalcet conc. mg/mL | pH | D(4, 3) |
| 0.05% | 0 | 0 (placebo) | 8.82 | 0.38 | 0 (placebo) | 8.82 | 0.38 |
| | 2 | 0 (placebo) | 8.63 | 0.39 | 0 (placebo) | 8.56 | 0.39 |
| | 4 | 0 (placebo) | 8.63 | 0.40 | 0 (placebo) | 8.39 | 0.40 |
| | 6 | 0 (placebo) | 8.68 | 0.39 | 0 (placebo) | 8.24 | 0.39 |
| | 8 | 0 (placebo) | 8.73 | 0.40 | 0 (placebo) | 8.24 | 0.40 |
| | 12 | 0 (placebo) | 8.66 | 0.38 | 0 (placebo) | 8.03 | 0.38 |
| | 0 | 4.42 | 8.77 | 0.39 | 4.42 | 8.77 | 0.39 |
| | 2 | 4.14 | 8.64 | 0.39 | 4.15 | 8.46 | 0.39 |
| | 4 | 4.35 | 8.65 | 0.40 | 4.30 | 8.36 | 0.40 |
| | 6 | 4.28 | 8.59 | 0.76 | 4.28 | 8.25 | 0.39 |
| | 8 | 4.43 | 8.67 | 0.40 | 4.39 | 8.29 | 0.43 |
| | 12 | 4.29 | 8.58 | 0.40 | 4.31 | 8.12 | 0.43 |
| 0.30% | 0 | 0 (placebo) | 9.23 | 0.39 | 0 (placebo) | 9.23 | 0.39 |
| | 2 | 0 (placebo) | 9.12 | 0.39 | 0 (placebo) | 9.03 | 0.39 |

TABLE 9-continued

| Storage conditions | | 5° C. | | | 40° C. | | |
|---|---|---|---|---|---|---|---|
| Buffer conc. | Time (weeks) | Cinacalcet conc. mg/mL | pH | D(4, 3) | Cinacalcet conc. mg/mL | pH | D(4, 3) |
| | 4 | 0 (placebo) | 9.16 | 0.40 | 0 (placebo) | 9.04 | 0.39 |
| | 6 | 0 (placebo) | 9.13 | 0.39 | 0 (placebo) | 8.98 | 0.40 |
| | 8 | 0 (placebo) | 9.20 | 0.40 | 0 (placebo) | 9.00 | 0.40 |
| | 12 | 0 (placebo) | 9.12 | 0.38 | 0 (placebo) | 8.81 | 0.39 |
| | 0 | 4.78 | 9.12 | 0.36 | 4.78 | 9.12 | 0.36 |
| | 2 | 4.60 | 9.07 | 0.35 | 4.58 | 8.98 | 0.36 |
| | 4 | 4.67 | 9.12 | 0.37 | 4.73 | 8.99 | 0.36 |
| | 6 | 4.60 | 9.11 | 0.37 | 4.65 | 8.93 | 0.36 |
| | 8 | 4.79 | 9.15 | 0.37 | 4.83 | 8.95 | 0.37 |
| | 12 | 4.66 | 9.08 | 0.36 | 4.71 | 8.81 | 0.38 |

EXAMPLE 5

This Example illustrates the effect of storage temperature on long-term stability of the formulations of the invention as measured by pH and the size of the droplets.

Calcimimetics emulsions for long-term studies were prepared at 5 mg/mL drug concentration, 5% SBO, 2% egg lecithin, 2% glycerin, 20 mM TRIS buffer at pH 9. The emulsions were packed in glass vials at 20 mL each and stored inverted in stability chambers. At each time-point, 3 vials from each chamber were pulled and analyzed for the calcimimetic concentration, pH and particle size. The pH and particle size data for cinacalcet are given in Table 10. The cinacalcet assay and impurity levels were within specifications for 2 years at 5° C. and 25° C. storage conditions, and for 9 months at 40° C. conditions. No significant changes were seen in particle size for 2 years at 5° C. and 25° C. and for 18 months at 40° C. The values for pH dropped over time, with greater magnitude of drop seen at higher temperature. There was no significant difference between the pH of the placebo as compared to that of the cinacalcet emulsions. The emulsions thus demonstrated long-term stability on storage.

TABLE 10

| | 5 mg/mL cinacalcet emulsion Storage condition | | | Placebo emulsion Storage condition | | |
|---|---|---|---|---|---|---|
| Time | 5° C. | 25° C. | 40° C. | 5° C. | 25° C. | 40° C. |
| | Measurement of pH | | | | | |
| Initial | 8.94 | 8.94 | 8.94 | 8.96 | 8.96 | 8.96 |
| 3 months | 8.86 | 8.89 | 8.73 | 8.92 | 8.82 | 8.65 |
| 6 months | 8.69 | 8.59 | 8.30 | 8.67 | 8.48 | 8.27 |
| 9 months | 8.63 | 8.48 | 8.15 | 8.71 | 8.45 | 8.04 |
| 12 months | 8.65 | 8.44 | 8.03 | 8.67 | 8.45 | 7.65 |
| 18 months | 8.84 | 8.59 | 7.93 | 8.80 | 8.45 | 7.85 |
| 24 months | 8.68 | 8.41 | 7.60 | 8.74 | 8.43 | 7.66 |
| | Measurement of average Particle Size[a], D(4, 3) in μm | | | | | |
| Initial | 0.150 | 0.150 | 0.150 | 0.165 | 0.165 | 0.165 |
| 3 months | 0.155 | 0.154 | 0.156 | 0.167 | 0.169 | 0.169 |
| 6 months | 0.155 | 0.158 | 0.150 | 0.16 | 0.164 | 0.163 |
| 12 months | 0.147 | 0.146 | 0.148 | 0.169 | 0.170 | 0.174 |
| 18 months | 0.148 | 0.147 | 0.150 | 0.170 | 0.170 | 0.176 |
| 24 months | 0.147 | 0.169 | — | 0.169 | 0.170 | — |

[a]Particle size measurements done using a Malvern Mastersizer 2000.

Similar results were seen on long-term stability studies for Compound A. Table 11 summarizes the effect of long term storage on pH and particle size of Compound A emulsions. No change in particle size was seen over a period of 14 months at any of the storage conditions tested. The pH drop was seen on storage similar to cinacalcet emulsions, with greater magnitude of pH reduction seen at higher temperature.

TABLE 11

| | 2 mg/mL Compound A emulsion Storage condition | | | 4 mg/mL Compound A emulsion Storage condition | | |
|---|---|---|---|---|---|---|
| Time | 5° C. | 25° C. | 40° C. | 5° C. | 25° C. | 40° C. |
| | Measurement of pH | | | | | |
| Initial | 9.1 | 9.1 | 9.1 | 9.1 | 9.1 | 9.1 |
| 1 months | 9.0 | 8.9 | 8.8 | 9 | 8.8 | 8.7 |
| 3 months | 8.9 | 8.7 | 8.5 | 8.8 | 8.6 | 8.4 |
| 6 months | 8.9 | 8.7 | 8.3 | 8.8 | 8.6 | 8.3 |
| 14 months | 8.9 | 8.7 | 8.1 | 8.9 | 8.6 | 8.1 |
| | Measurement of average Particle Size, D(4, 3) in μm | | | | | |
| Initial | 0.2 | 0.2 | 0.2 | 0.2 | 0.2 | 0.2 |
| 1 months | 0.2 | 0.2 | 0.2 | 0.2 | 0.2 | 0.2 |
| 3 months | 0.2 | 0.2 | 0.2 | 0.2 | 0.2 | 0.2 |
| 6 months | 0.2 | 0.2 | 0.2 | 0.2 | 0.2 | 0.2 |
| 14 months[a] | 0.14 | 0.14 | 0.14 | 0.14 | 0.14 | 0.14 |

[a]Measurements done using a Malvern Mastersizer 2000. All other measurements done using a Malvern Mastersizer S. The lower number is due to the differences in instrument.

EXAMPLE 6

This Example illustrates the protective effect of the formulations of the invention as measured by irritation in the rabbit ear vein (REV). A typical protocol for evaluation of the local tolerance for formulations was as follows.

Dosing of animals. The rabbits used were male New Zealand rabbits weighing approximately 2.5 to 4 kg. The rabbits were acclimatized for a period of 10 days following receipt before the start of the study. The rabbits were randomized into groups based on the number of formulations to be studied. Typically 3 rabbits were used per group.

For each group of rabbits, the formulation containing the drug to be tested was dosed in the right marginal ear vein, with the corresponding placebo being dosed at the same time in the left marginal ear vein. The placebos were prepared such that they matched the formulation composition, and the technique of dosing for the drug formulations and the placebo formulations were kept the same. Typical dosing volumes ranged from 1 mL/kg to 5 mL/kg. The formulations were either dosed as (a) bolus injection wherein the entire dosing volume was administered within 5 minutes; (b) 30 minute infusion; or (c) a 2 hour infusion. The formulations were administered through appropriately sized syringes and catheters. The injection sites were marked with indelible ink for identification at each observation period. The rabbits were dosed based upon the Day 1 body weight.

Observation of animals. Each animal was observed cage side at least twice daily for mortality/morbundity. Each animal received a detailed clinical observation once prior to randomization, once prior to dosage administration and once daily thereafter.

Each injection site was observed for redness and swelling prior to dosing and at approximately 4, 24 and 48 hours post dose. Any abnormalities were recorded as they were observed. Observations for local irritation were scored according to the following scale

| Erythema (redness) | |
|---|---|
| No Erythema | 0 |
| Very slight erythema (barely perceptible) | 1 |
| Well-defined erythema | 2 |
| Moderate to severe erythema | 3 |
| Severe erythema (beet redness to slight eschar formation, injuries in depth, necrosis) | 4 |

-continued

| Edema (swelling) | |
|---|---|
| No Edema | 0 |
| Very slight edema (barely perceptible) | 1 |
| Slight edema (edges of area are well defined by definite rising) | 2 |
| Moderate edema (raised approximately 1 mm) | 3 |
| Severe edema (raised beyond 1 mm and extending beyond area of exposure) | 4 |

At each interval the area of irritation (if present) was also measured. The actual length and width in mm was recorded.

On day 3 the animals were euthanized and the tissues from the Pinna of the left and right ear, and any gross lesions (if present) of the ear or ear vein were collected. Histopathology was performed on the collected tissues. After fixation, the pinna was tripped into a total of 4 sections of 1 cm each; one of which included the deposition site (location of the end of the catheter in the ear) and one from approximately 1-, 2-, and 3-cm downstream from the deposition site. Each section included skin, cartilage, vein and other soft tissue. These tissues were then embedded in paraffin, sectioned and stained with hematoxylin and eosin, and examined via light microscopy.

The data summarized in Table 12 demonstrate that when cinacalcet is administered IV as a solution, it is poorly tolerated and causes mild to moderate local venous toxicity (as measured in a solution formulation consisting of acetate mannitol buffer at pH 4). This is seen macroscopically by the presence of erythema and edema in the ears of the rabbits dosed with the solution, and microscopically on histological examination by presence of mixed inflammatory cells, perivascular edema, hemorrhage and thrombosis. These effects are more severe when Cinacalcet is dosed slowly, as a 2 hour infusion as compared to a bolus injection. However, in the cinacalcet-containing emulsions of the invention these effects were greatly reduced or completely eliminated.

TABLE 12

| Treatment | Dose | Time (h) | Erythema | Edema | Histopathology |
|---|---|---|---|---|---|
| Cinacalcet solution in acetate mannitol buffer, pH 4, Bolus dose | Placebo | 0 | 0.0 ± 0.0 | 0.0 ± 0.0 | Mnimal to mild infiltrates of mixed |
| | | 48 | 0.0 ± 0.0 | 0.0 ± 0.0 | inflammatory cells, minimal to moderate |
| | Cinacalcet 2 mg/kg (conc. 0.5 mg/mL) | 0 | 0.0 ± 0.0 | 0.0 ± 0.0 | perivascular edema and hemorrage, |
| | | 48 | 2.7 ± 0.6 | 1.7 ± 0.6 | occasional vascular thrombosis. Higher |
| | Cinacalcet 2 mg/kg (conc. 1 mg/mL) | 0 | 0.0 ± 0.0 | 0.0 ± 0.0 | incidence and severity compared to placebo. |
| | | 48 | 2.7 ± 0.6 | 2.0 ± 1.7 | Mild to severe effects seen at the higher dose. |
| Cinacalcet solution in acetate mannitol buffer, pH 4, 2 hour infusion | Placebo | 0 | 0.0 ± 0.0 | 0.0 ± 0.0 | The cinacalcet treated ears were most |
| | | 48 | 0.3 ± 0.6 | 0.0 ± 0.0 | severely affected compared to the placebo. |
| | Cinacalcet 2 mg/kg (conc. 0.5 mg/mL) | 0 | 0.0 ± 0.0 | 0.0 ± 0.0 | The injection sites of all these animals show |
| | | 48 | 4.0 ± 0.0 | 3.3 ± 1.2 | mild to severe acute, necrotizing inflammation at all sites tested. Minimal to mild thrombosis |

The results of acute local venous toxicity study for cinacalcet in an emulsion formulation at pH 9 are summarized in Table 13.

TABLE 13

| Treatment | Dose | Time (h) | Erythema | Edema | Histopathology |
|---|---|---|---|---|---|
| Cinacalcet in emulsion with TRIS buffer 20 mM, pH 9, 2-hour infusion | Placebo | 0 | 0.0 ± 0.0 | 0.0 ± 0.0 | Intravenous adminstration of cinacalcet in the |
| | | 48 | 0.0 ± 0.0 | 0.0 ± 0.0 | lipid emulsion was well tolerated as a 2 hour |
| | Cinacalcet 2 mg/kg (conc. 0.5 mg/mL) | 0 | 0.0 ± 0.0 | 0.0 ± 0.0 | infusion. Predominant microscopic finding |
| | | 48 | 0.0 ± 0.0 | 0.0 ± 0.0 | was dilated veins, which cocurred in both placebo and cinacalcet treated ears |

There results presented in Table 13 demonstrate that when cinacalcet formulated in the emulsion containing TRIS is dosed as an infusion, the emulsion is well tolerated with no significant macroscopic or microscopic findings. This demonstrates the ability of the emulsion formulation to have a protective effect on vasculature when the emulsions are dosed IV.

Table 14 summarizes the results for the acute local venous toxicity study for compound A in a solution formulation and an emulsion formulation.

TABLE 14

| Treatment | Dose | Time (h) | Erythema | Edema | Histopathology |
|---|---|---|---|---|---|
| Compound A in solution in acetate mannitol buffer, pH 4, 2 hour infusion | Placebo | 0 | 0.0 ± 0.0 | 0.0 ± 0.0 | Severity and incidence of edema, hemorrhage and subacute inflammation was higher in the ears treated with Compound A compared to placebo |
| | | 48 | 0.0 ± 0.0 | 0.0 ± 0.0 | |
| | Compound A at 1 mg/kg (conc. 0.1 mg/mL) | 0 | 0.0 ± 0.0 | 0.0 ± 0.0 | |
| | | 48 | 1.3 ± 2.3 | 0.0 ± 0.0 | |
| Compound A in emulsion with TRIS buffer 20 mM, pH 9, 2-hour infusion | Placebo | 0 | 0.0 ± 0.0 | 0.0 ± 0.0 | Severity and incidence of edema, hemorrhage and subacute inflammation was much lower in all thee animals as compared to the solution. No significant difference seen in the ears treated with emulsion containing Compound A as compared to placebo at either dose. |
| | | 48 | 7.0 ± 0.0 | 0.0 ± 0.0 | |
| | Compound A at 2 mg/kg (conc. 5 mg/mL) | 0 | 0.0 ± 0.0 | 0.0 ± 0.0 | |
| | | 48 | 0.0 ± 0.0 | 0.0 ± 0.0 | |
| | Compound A at 6 mg/kg (conc. 5 mg/mL) | 0 | 0.0 ± 0.0 | 0.0 ± 0.0 | |
| | | 48 | 0.0 ± 0.0 | 0.0 ± 0.0 | |

These results demonstrate that Compound A when dosed as a solution, shows evidence of local venous toxicity similar to cinacalcet. However, an emulsion containing Compound A has a protective effect on the vasculature and thus higher doses of the compound can be dosed without local venous toxicity.

The results summarized in Table 15 show that cinacalcet can be injected as an emulsion buffered with either TRIS or DEA and dosed as bolus. Emulsions containing either buffer are well tolerated (as compared to the solutions in Table 12). The local irritation effects observed when TRIS buffered emulsions are dosed are minimal to mild, and are seen only at the injection site, indicating that they are due to the insertion of the catheter in the vein and not related to the formulations being dosed.

TABLE 15

| Treatment | Dose | Time (h) | Erythema | Edema | Histopathology |
|---|---|---|---|---|---|
| Cinacalcet in emulsion with TRIS buffer 5 mM, pH 9, Bolus dose | Placebo | 0 | 0.0 ± 0.0 | 0.0 ± 0.0 | Minimal to mild perivascular acute inflammatory changes observed for both placebo and cinacalcet emulsions containing TRIS. These were mostly at the deposition site of the catheter. |
| | | 48 | 0.0 ± 0.0 | 0.0 ± 0.0 | |
| | Cinacalcet 2 mg/kg (conc. 10 mg/mL) | 0 | 0.0 ± 0.0 | 0.0 ± 0.0 | |
| | | 48 | 0.0 ± 0.0 | 0.0 ± 0.0 | |
| Cinacalcet in emulsion with DEA buffer 0.05%, pH 9, Bolus dose | Placebo | 0 | 0.0 ± 0.0 | 0.0 ± 0.0 | Mild to moderate perivascular acute necrotizing inflammation observed for both placebo and cinacalcet emulsions containing DEA. |
| | | 48 | 0.7 ± 1.2 | 0.0 ± 0.0 | |
| | Cinacalcet 2 mg/kg (conc. 10 mg/mL) | 0 | 0.3 ± 0.6 | 0.0 ± 0.0 | |
| | | 48 | 0.0 ± 0.0 | 0.0 ± 0.0 | |

EXAMPLE 7

This Example illustrates the protective effect of the emulsions of the invention as demonstrated by preventing loss in drug strength due to adsorption to tubing used in the clinical setting.

Figure 3:
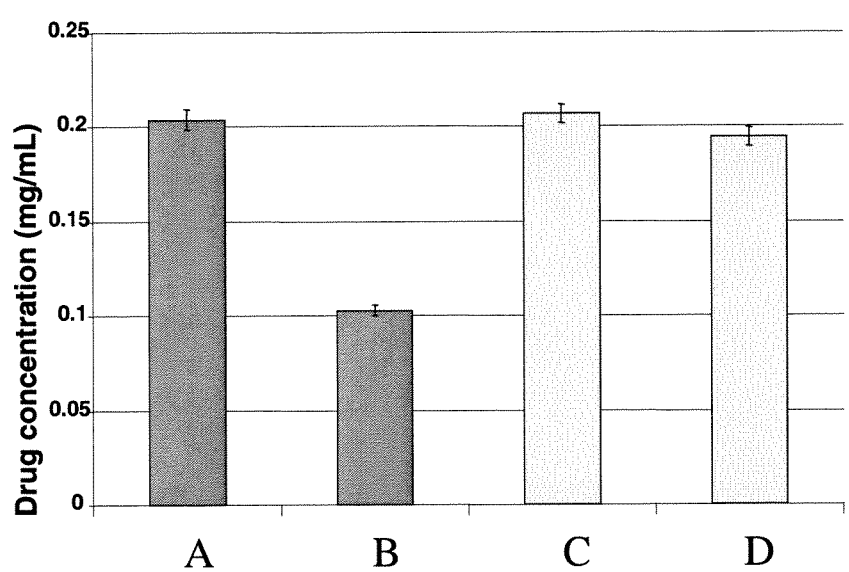
FIG. 3 demonstrates that the emulsions of the invention are not adsorbed in the tubing after 1 hour of exposure as compared to drug-containing solutions during the same exposure.

A solution of compound A was prepared in acetate mannitol buffer at pH 4. At this pH, the compound forms a clear solution of concentration 0.2 mg/mL. An equivalent emulsion was prepared at the same concentration with 5% soybean oil, 2% lecithin, 2% glycerin and 20 mM TRIS buffer at pH 9. PVC tubing was selected as an example of commonly used intravenous infusion set. 15 cm sections of this tube were filled with either the solution or emulsion formulation and clamped on both ends. These filled tubes were held at the ambient temperature for 1 hour. The formulations inside were collected and analyzed for drug content using reversed phase HPLC. FIG. 3 demonstrates that the emulsions of the invention are not adsorbed in the tubing after 1 hour of exposure as compared to drug-containing solutions during the same exposure. For the solution, the drug concentration after 1 hour holding in the tubing was found to be about 50% of initial concentration. For the emulsion, there was no significant difference in concentration of drug before or after exposure to tubing. Panel A: Compound A in acetate/mannitol solution, pre-exposure. Panel B: compound A in acetate/mannitol solution, after 1 hour of exposure to the PVC tubing. Panel C: compound A formulated in the emulsion of the invention, pre-exposure. Panel D: compound A formulated in the emulsion of the invention, pre-exposure, after 1 hour of exposure to the PVC tubing.

EXAMPLE 8

The present Example illustrates the use of a fatty acid salt as a droplet charge modifier of emulsions containing an exemplary drug composition. More particularly, the present example shows the use of sodium oleate as a droplet charge modifier for Cinacalcet emulsions.

Materials: Soy bean oil and egg lecithin was obtained from Lipoid Inc. Sodium oleate was obtained from Sigma chemicals. All other lab chemicals were similar to that described under materials section.

Preparation of Each Emulsion: the Emulsion were Prepared Using Substantially the same method as discussed above in Example 2 under "Laboratory scale preparation." Briefly, the aqueous phase was prepared by adding appropriate amounts of glycerin and water to an appropriate container. The glycerin and water were mixed well and maintained at elevated temperatures (60-70° C.) by immersing the container in a water batch.

The oil phase was prepared by adding appropriate oil and lecithin. The container was tared and the cinacalcet free base was added. Appropriate quantity of sodium oleate (between 0-1%) was added to this oil phase mixture. The oil/lecithin/cinacalcet mixture was mixed at an elevated temperature using sonicater probes to disperse/dissolve the lecithin, the Cinacalcet free base and the sodium oleate.

The hot oil phase was transferred to the aqueous phase at elevated temperatures and homogenized to obtain coarse emulsion. Fine emulsion was obtained using a microfluidizer.

Charge Measurement: Zeta-potential as a function of pH was determined using a Malvern Zetasizer Nano Series Model ZEN 3600 laser-scattering particle electrophoretic analyzer that measures the electrophoretic mobility and zeta potential distribution. Samples were prepared for the zeta potential titration by diluting each emulsion approximately 2500-fold in water. The pH of this mixture was noted after dilution, and then adjusted to a pH 9 using sodium hydroxide. The pH was then titrated down to pH 6 in 0.3 or 0.5 unit steps. Zeta potential measurements were taken at every step. The zeta-potential of each emulsion was plotted as a function of pH and fit to a linear regression line. Using this regression line the pH at which the emulsion had a zeta potential of zero was determined.

Zeta-potential is a measure of the charge on the emulsion droplets. The charge on the droplets contributes to the stability of the emulsions due to charge-charge repulsion of the droplets. These forces thus hinder the droplets from coalescing. Thus, it has been found that the higher the magnitude of charge on the droplets, the better the expected stability of the emulsion.

Figure 4:
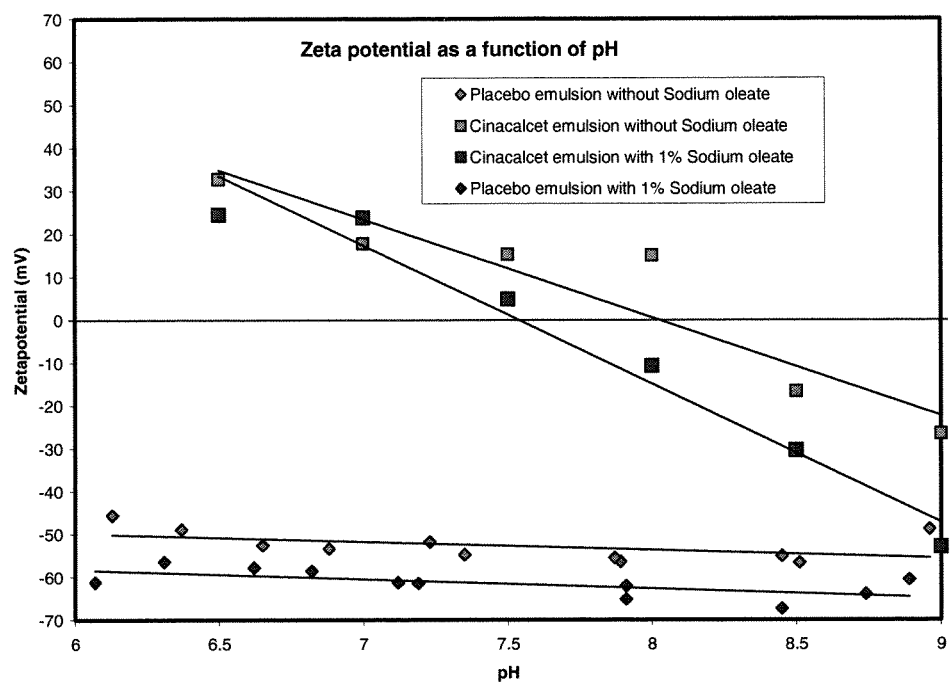
FIG. 4 illustrates zeta potential vs. pH curve for Cinacalcet emulsions as compared to the placebo emulsion in presence of a charge stabilizer such as sodium oleate.

Use of lecithin as the emulsifier imparts a negative charge to the emulsion droplets in the absence of drug. However, compounds like cinacalcet can interfere with the charge characteristics of the emulsion. It is noted that at lower pH values, the compound is ionized carrying a net positive charge. In this charged state it can exist at the oil water interface (similar to a surface active agent). Without being bound to a particular theory or mechanism of action, it is thought that in this charged state at the interface, the charged drug possibly has a neutralizing effect on the negative charge imparted by lecithin. This phenomenon can be observed by measuring the zeta-potential of the emulsions as a function of pH (Zeta-titration). A typical zeta-titration curve for an emulsion containing cinacalcet compared to its corresponding placebo is shown in FIG. 4.

It is observed that for the blank emulsion, although there is some change in the zeta potential with decreasing pH, the overall zeta potential is negative over the pH range studied (6-9). However, for an emulsion containing cinacalcet at pH 9 the zeta-titration curve is significantly different. At pH 9, where cinacalcet would be predominantly unionized, the zeta potential is negative. However, as the pH is lowered, the zeta potential increases until finally at pH 8, it is in the positive range. Linear regression of this data shows good correlation coefficient with a negative slope. The X-intercept, i.e., the pH at which the zeta-potential is zero is the pH of zero-Zeta. At this pH, the overall charge on the droplets is expected to be zero and the emulsion will be unstable. To improve stability of the emulsions, charge modifiers such as sodium oleate can be added which can contribute to the negative charge on these emulsions. It is seen in FIG. 4 that in presence of sodium oleate, the zeta potential of the emulsion is more negative at the measured values of pH.

The zeta-potential data at various pH for cinacalcet emulsions containing varying amounts of sodium oleate are summarized in Table 16.

TABLE 16

| | % Na Oleate | | | |
|---|---|---|---|---|
| pH | 0 | 0.25 | 0.5 | 1 |
| 9.0 | −26.5 | −42.5 | −42.1 | −52.9 |
| 8.5 | −16.7 | −10 | −26.8 | −30.4 |
| 8.0 | 15 | 2.83 | 0.242 | −10.7 |

TABLE 16-continued

| | % Na Oleate | | | |
|---|---|---|---|---|
| pH | 0 | 0.25 | 0.5 | 1 |
| 7.5 | 15.3 | 7.24 | 16.2 | 4.87 |
| 7.0 | 17.8 | 28.1 | 27.8 | 23.8 |
| 6.5 | 32.8 | 36 | 37.4 | 24.5 |
| pH at which charge is zero | 8.02 | 7.87 | 7.81 | 7.54 |

It is seen that above pH 8.5 when cinacalcet is predominantly un-ionized, the sodium oleate contributes to the negative charge on the emulsion droplets. At pH 9, the negative charge on the emulsion droplets is much higher for the emulsion containing 1% sodium oleate as compared to that without sodium oleate. The presence of sodium oleate also has an effect on the pH at which the charge on the emulsion droplets is zero. Emulsions containing sodium oleate reach neutral zeta potential at a lower pH value. These would be expected to be stable over a broader range of pH.

While the present example is demonstrated using sodium oleate as a charge modifier and cinacalcet as the drug agent, the experimental protocol set forth in this example may be readily be repeated with any fatty acid that it may be desirable to use as a charge modifier. Such fatty acids may include oleic acid, linoleic acid, stearic acid, palmitic acid, decanoic acid, lauric acid, myristic acid, icosanoic acid, behenic acid, myristoleic acid, palmitoleic acid, alpha linolenic acid, arachidonic acid, eicosapentanoic acid, and salts thereof and also combinations of two or more of these fatty acids. In addition or as an alternative, other acids may be used, such as for example, hydrochloric acid, tartaric acid, benzoic acid, citric acid, and salts thereof. Likewise while cinacalcet is used as the drug in this specific example, any other agent to be delivered in the stable emulsions of the invention also may be readily tested using the protocol set forth above.

EXAMPLE 9

This example illustrates the effect of pH on the emulsion droplet charge of the calcimimetic compound (1R)-1-(6-(methyloxy)-4'-(trifluoromethyl)-3-biphenylyl)-N-((1R)-1-phenylethyl)ethanamine.

Materials: Soybean oil and lecithin was obtained from Lipoid, Inc. Phosal 53 MCT was obtained from American Lecithin Company (now a subsidiary of Lipoid, Inc.). Water For Irrigation was obtained from Baxter, and glycerin was obtained from (JT. Baker).

Emulsion Preparation: The emulsions were prepared using essentially the same method as discussed in Example 2 under Lab scale preparation.

The aqueous phase was prepared by combining appropriate amounts of glycerin and water to an appropriate container, mixing and heating to a temperature of 50-80° C. on a stirrer/hot plate.

The oil phase was prepared by adding appropriate oil, lecithin and compound, or Phosal 53 MCT and compound, to an appropriate container and sonicated with a sonicating probe to an elevated temperature and until everything was well dispersed.

The oil phase was quickly added to the hot aqueous phase and this mixture was sonicated with a sonicated probe for several minutes, rendering the final emulsion.

Using a Malvern Mastersizer 2000, Particle-size was determined to be <1 μm for each emulsion. Zeta-potential as a function of pH was determined using a Malvern Zetasizer Nano Series Model ZEN 3600, equipped with a Multi Purpose Titrator, MPT-2.

Figure 5:
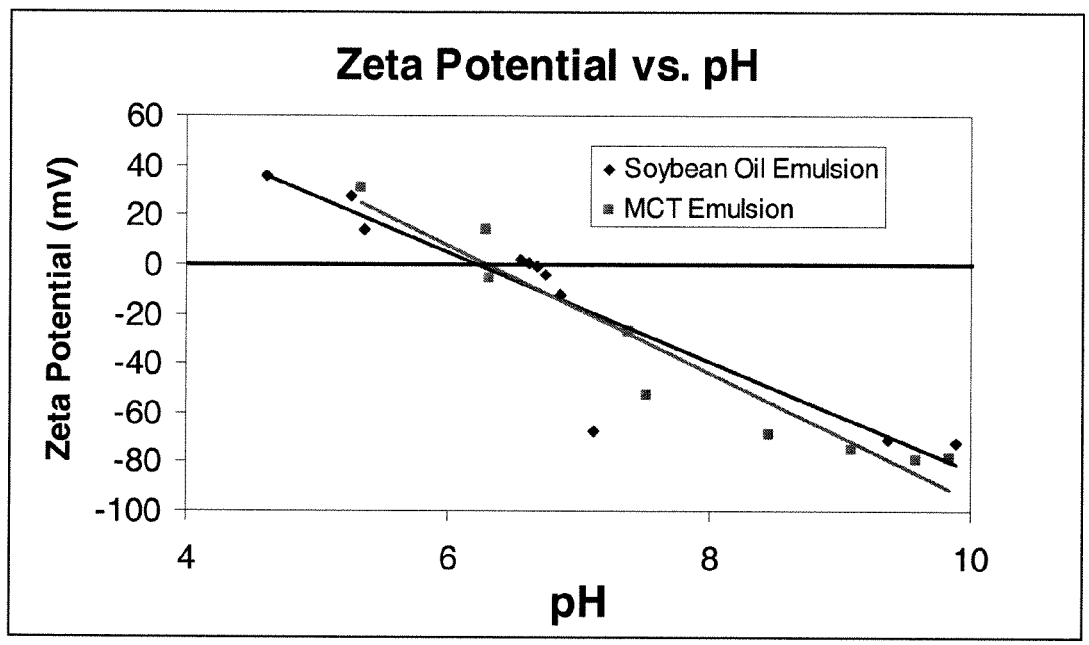
FIG. 5 shows that the droplet charge of each emulsion is dependent on pH.

As the data in FIG. 5 demonstrate, the droplet charge of each emulsion is dependent on its pH, with a pH of zero-zeta being observed. Example 3 clearly demonstrates the relationship between pH, zeta and emulsion stability, suggesting that a pH or charge stabilizer would extend the stability of these emulsions.

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A pharmaceutical formulation comprising:
   an oil phase from 1 to 30% by weight containing cinacalcet freebase from 0.001 to 5% by weight;
   a phospholipid emulsifier from 0.1 to 5% by weight; and
   an aqueous phase containing a charge stabilizer,
   wherein the formulation is stable and has a protective effect against irritation caused by the cinacalcet freebase.

2. The formulation of claim 1, wherein the phospholipid emulsifier is an egg lecithin, egg yolk phospholipids, soy lecithin or soybean phospholipids.

3. The formulation of claim 1, wherein the charge stabilizer is TRIS buffer in a concentration from 5 to 20 mM.

4. The formulation of claim 1, wherein the charge stabilizer is diethanolamine buffer from 0.05 to 0.3% by weight.

5. The formulation of claim 1, wherein the cinacalcet freebase is present in an amount from 0.001-110 mg/mL.

6. The formulation of claim 1, further comprising glycerol.

7. The formulation of claim 1, wherein pH of the formulation is from 7 to 9.5.

8. The formulation of claim 1, wherein pH of the formulation is from 8.0 to 9.5.

9. The formulation of claim 1 further comprising at least one preservative, antioxidant, buffering agent, acidifying agent, alkalizing agent, antibacterial agent, antifungal agent, solubility enhancing agent, complexation enhancing agent, organic solvent, electrolyte, salt, stabilizer, tonicity modifier, antifoaming agent, or a combination thereof.

10. The formulation of claim 9, wherein the stabilizer is oleic acid, linoleic acid, stearic acid, palmitic acid, decanoic acid, lauric acid, myristic acid, icosanoic acid, behenic acid, myristoleic acid, palmitoleic acid, alpha linolenic acid, arachidonic acid, eicosapentanoic acid, and salts thereof.

11. The formulation of claim 1, wherein the formulation is stable at temperatures from about 5° C. to about 40° C.

12. The formulation of claim 1, wherein the formulation is stable during and after autoclaving.

13. The formulation of claim 1 further comprising one or more local anesthetic agents.

14. The formulation of claim 13, wherein the local anesthetic agent is benzocaine or procaine.

15. A pharmaceutical formulation comprising an oil-in-water emulsion, said emulsion comprises an oil phase from 1 to 30% by weight of said emulsion containing:
   from 0.001 to 5% by weight of cinacalcet freebase that typically causes irritation at the point of administration compound;
   from 0.1 to 5% by weight of a phospholipid emulsifier; and
   an aqueous phase containing a charge stabilizer,
   wherein said emulsion contains droplets that have an overall negative surface charge.

16. The pharmaceutical formulation of claim 15, wherein said phospholipid emulsifier is an egg lecithin, egg yolk phospholipids, soy lecithin or soybean phospholipids.

17. The pharmaceutical formulation of claim 15, wherein said phospholipids emulsifier comprises a phospholipids agent selected from the group consisting of 1,2-Dilauroyl-sn-glycerol (DLG), 1,2-Dimyristoyl-sn-glycerol (DMG), 1,2-Dipalmitoyl-sn-glycerol (DPG), 1,2-Distearoyl-sn-glycerol (DSG); phosphatidic acids such as 1,2-Dimyristoyl-sn-glycero-3-phosphatidic acid, sodium salt (DMPA,Na), 1,2-Dipalmitoyl-sn-glycero-3-phosphatidic acid, sodium salt (DPPA,Na), 1,2-Distearoyl-sn-glycero-3-phosphatidic acid, sodium salt-(DSPA,Na); phosphatidylcholines such as 1,2-Dilauroyl-sn-glycero-3-phosphocholine (DLPC), 1,2-Dimyristoyl-sn-glycero-3-phosphocholine (DMPC), 1,2-Dipalmitoyl-sn-glycero-3-phosphocholine (DPPC), 1,2-Dipalmitoyl-sn-glycero-3-phosphocholine (DPPC), 1,2-Distearoyl-sn-glycero-3-phosphocholine (DSPC), 1,2-Distearoyl-sn-glycero-3-phosphocholine (DSPC); phosphatidylethanolamines such as 1,2-Dilauroyl-sn-glycero-3-phosphoethanolamine (DLPE), 1,2-Dimyristoyl-sn-glycero-3-phosphoethanolamine (DMPE), 1,2-Dipalmitoyl-sn-glycero-3-phosphoethanolamine (DPPE), 1,2-Distearoyl-sn-glycero-3-phosphoethanolamine (DSPE); phosphatidylclyerols such as 1,2-Dilauroyl-sn-glycero-3-phosphoglycerol, sodium salt (DLPG), 1,2-Dimyristoyl-sn-glycero-3-phosphoglycerol, sodium salt (DMPG), 1,2-Dimyristoyl-sn-glycero-3-phospho-sn-1-glycerol, ammonium salt (DMP-sn-1-G,NH4), 1,2-Dipalmitoyl-sn-glycero-3-phosphoglycerol, sodium salt (DPPG,Na), 1,2-Distearoyl-sn-glycero-3-phosphoglycerol, sodium salt (DSPG,Na), 1,2-Distearoyl-sn-glycero-3-phospho-sn-1-glycerol, sodium salt (DSP-sn-1G,Na), phosphatidylserines such as 1,2-Dipalmitoyl-sn-glycero-3-phospho-L-serine, sodium salt (DPPS,Na), 1-Palmitoyl-2-oleoyl-sn-glycero-3-phosphocholine (POPC), 1-Palmitoyl-2-oleoyl-sn-glycero-3-phosphoglycerol, sodium salt (POPG,Na), 1-Palmitoyl-2-oleoyl-sn-glycero-3-phosphoglycerol, ammonium salt (POPG,NH4), 1-Palmitoyl-2-lyso-sn-glycero-3-phosphocholine (P-lyso-PC) and 1-Stearoyl-2-lyso-sn-glycero-3-phosphocholine (S-lyso-PC) and combinations thereof.

18. The pharmaceutical formulation of claim 15, wherein the charge stabilizer is a buffer, an acid or a salt thereof.

19. The pharmaceutical formulation of claim 18, wherein the buffer is selected from the group consisting of diethanolamine, glycine, citrate, acetate, histidine, phosphate, carbonate, meglumine, N-methyl glucamine and tris(hydroxymethyl) aminomethane (TRIS) buffers.

20. The pharmaceutical formulation of claim 18, wherein the acid or the salt thereof is selected from the group consisting of hydrochloric acid, tartaric acid, benzoic acid, citric acid, decanoic acid, lauric acid, myristic acid, palmitic acid, stearic acid, icosanoic acid, behenic acid, myristoleic acid, palmitoleic acid, oleic acid, linoleic acid, alpha linolenic acid, arachidonic acid, eicosapentanoic acid, and salts thereof.

21. The pharmaceutical composition of claim 15, wherein the oil phase comprises a vegetable oil or a hydrogenated vegetable oil.

22. The pharmaceutical composition of claim 21, wherein the vegetable or the hydrogenated vegetable oil is selected from the group consisting of peanut oil, corn oil, castor oil, cottonseed oil, soybean oil, olive oil, safflower oil, peppermint oil, coconut oil and palm seed oil.

23. The pharmaceutical formulation of claim 15, wherein the oil phase is selected from the group consisting of beeswax, vitamin E, oleic acid, medium chain monoglycerides, diglycerides, triglycerides, structured triglycerides, and mixtures thereof.

24. The pharmaceutical formulation of claim 15, wherein the formulation is stable at temperatures from about 5° C. to about 40° C.

25. The pharmaceutical formulation of claim 15, wherein the formulation is stable after autoclaving.

26. A method of administering the formulation of claim 1 to a subject in need thereof wherein the administration is intravenous.

27. The method of claim 26, wherein the formulation is administered via infusion.

28. The method of claim 26, wherein the formulation is administered by bolus injection.

29. A method of preparing the formulation of claim 1 comprising the following steps:
 mixing the aqueous phase and the charge stabilizer;
 dissolving the cinacalcet freebase in the oil phase at an elevated temperature;
 mixing the oil phase from step (b) and the aqueous phase from step (a) and said emulsifier;
 homogenizing the formulation; and
 optionally adjusting pH.

30. A method of treating a subject in need of a calcimimetic comprising administering a therapeutically effective amount of a formulation of claim 1.

31. The method of claim 30, wherein said subject is suffering from hyperparathyroidism.

32. The method of claim 31 wherein said therapeutically effective amount decreases the levels of parathyroid hormone (PTH) in said subject.

33. The method of claim 30, wherein said subject is suffering from chronic kidney disease associated with elevated PTH levels and said therapeutically effective amount decreases the symptoms of kidney disease in said subject.

34. The method of claim 33, wherein said subject is suffering from hyperparathyroidism.

35. The method of claim 34, wherein said hyperparathyroidism is primary hyperparathyroidism.

36. The method of claim 34, wherein said hyperparathyroidism is secondary hyperparathyroidism.

37. The method of claim 30, wherein said subject is suffering from hypercalcemia.

38. The method of claim 30, wherein said therapeutically effective amount decreases the serum calcium levels of said subject as compared to the serum calcium levels of said subject in the absence of administration of said formulation.

39. The method of claim 30, wherein said therapeutically effective amount decreases the serum phosphorus levels of said subject as compared to the serum phosphorus levels of said subject in the absence of administration of said formulation.

40. The method of claim 30, wherein said subject is suffering from parathyroid carcinoma.

41. The method of claim 30, wherein said formulation is administered at a dose of about 20 mg per day to about 200 mg/day.

42. The method of claim 30, wherein said formulation is administered in combination with a composition comprising vitamin D or a vitamin D analog.

43. The method of claim 30, wherein said formulation is administered in combination with another calcimimetic.

44. The method of claim 30, wherein said formulation is administered in combination with a composition comprising an inhibitor of cytochrome P450 2D6.

45. The method of claim 30, wherein said subject is suffering from vascular calcification and said therapeutically effective amount decreases the formation, growth or deposition of extracellular matrix hydroxyapatite crystal deposits in the blood vessels of said subject.

46. The method of claim 45, wherein said subject is suffering from coronary, valvular, aortic, or other blood vessel calcification.

* * * * *